(12) United States Patent
Gupta et al.

(10) Patent No.: US 6,294,503 B1
(45) Date of Patent: Sep. 25, 2001

(54) FUSED HETEROCYCLE COMPOUNDS, PROCESS FOR THEIR PREPARATION, AND HERBICIDAL COMPOSITIONS CONTAINING THEM

(75) Inventors: Sandeep Gupta, Concord; Shao-Yong Wu, Willoughby Hills; Masamitsu Tsukamoto, Mayfield Hts.; Bai-Ping Ying, Concord; David A. Pulman, Mentor, all of OH (US)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 09/204,060

(22) Filed: Dec. 3, 1998

(51) Int. Cl.⁷ .......................... A01N 43/84; C07D 413/04
(52) U.S. Cl. ............................................ 504/225; 544/105
(58) Field of Search .............................. 544/105; 504/225

(56) References Cited

U.S. PATENT DOCUMENTS

| | | | |
|---|---|---|---|
| 4,734,124 | 3/1988 | Chang et al. | 544/105 |
| 4,761,174 | 8/1988 | Chang et al. | 71/92 |
| 5,084,084 | 1/1992 | Satow et al. | 71/92 |
| 5,281,571 | 1/1994 | Woodward et al. | 504/225 |

FOREIGN PATENT DOCUMENTS

| | | |
|---|---|---|
| 3927 438 A1 | 2/1991 | (DE). |
| 0 170 191 A2 | 2/1986 | (EP). |

OTHER PUBLICATIONS

Domagala et al., Chemical Astracts, vol. 130:338119, 1999.*
Tabusa et al., Chemical Astracts, vol. 120:298482, 1994.*
Ohmori et al., Chemical Astracts, vol. 120:244963, 1994.*
Kise et al., Chemical Astracts, vol. 115:114547, 1991.*
Tabusa et al., Chemical Astracts, vol. 109:6428, 1988.*

* cited by examiner

*Primary Examiner*—Richard L. Raymond
(74) *Attorney, Agent, or Firm*—Sughrue, Mion, Zinn, Macpeak & Seas, PLLC

(57) ABSTRACT

Novel fused heterocycle compounds represented by the formula (I) are described. Q, R, W, —L—X—, Y, Z, and n are as defined in the disclosure. Also described are the processes for the manufacture of these compounds and agriculturally suitable compositions containing these as active ingredients which are useful as herbicides for general or selective pre-emergent or post-emergent control of undesired plant species.

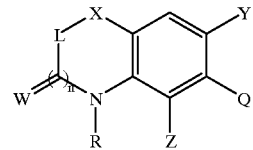

12 Claims, No Drawings

FUSED HETEROCYCLE COMPOUNDS, PROCESS FOR THEIR PREPARATION, AND HERBICIDAL COMPOSITIONS CONTAINING THEM

The present invention relates to fused heterocycle compounds, process for their preparation, and herbicidal compositions containing them.

BACKGROUND OF THE INVENTION

It is known that some benzoxazine compounds as herbicides. They are described in U.S. Pat. Nos. 4,734,124, 4,761,174, 5,084,084 or 5,281,571, European Patent publication No. 0170191 or German Patent publication No. 3927438.

However, it is not known that benzoxazine compounds introduced functional groups at position 5 of the benzoxazine ring.

SUMMARY OF THE INVENTION

This invention delineates a method for the control of undesired vegetation in a plantation crop by the application to the locus of the crop an effective amount of a compound described herein. The herbicidal compounds of the present invention are described by the following formula (I) or its salt:

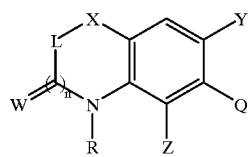

I wherein Q is a heterocycle selected from the group consisting of Q1 to Q24:

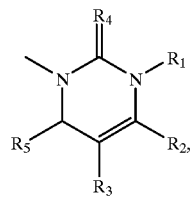

Q1

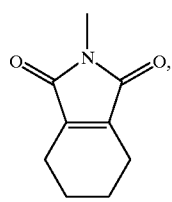

Q2

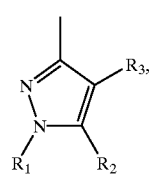

Q3

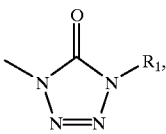

Q4

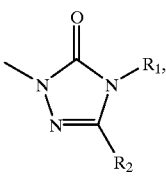

Q5

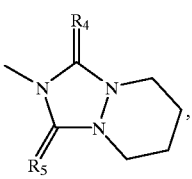

Q6

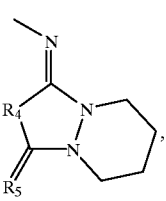

Q7

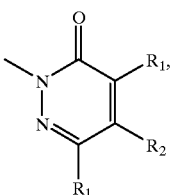

Q8

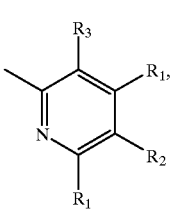

Q9

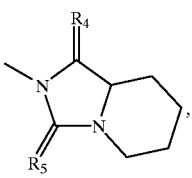

Q10

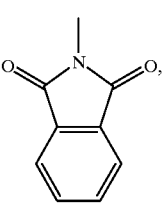

Q11

-continued

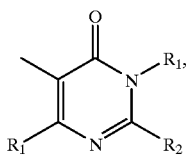
Q12

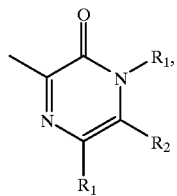
Q13

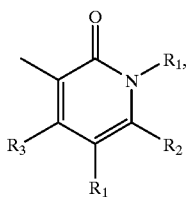
Q14

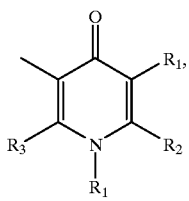
Q15

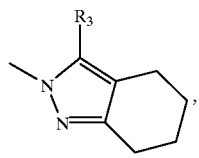
Q16

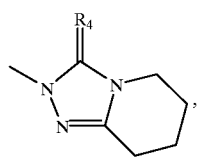
Q17

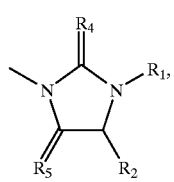
Q18

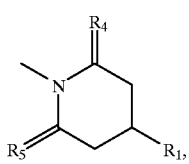
Q19

-continued

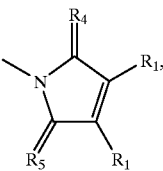
Q20

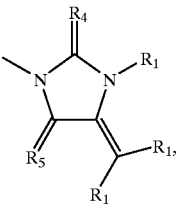
Q21

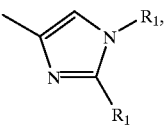
Q22

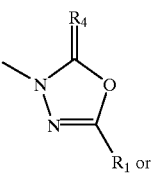
Q23

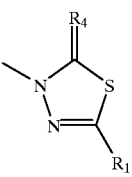
Q24 wherein $R_1$ is hydrogen, alkyl, haloalkyl, alkenyl, alkynyl, amino, alkoxyalkyl, acetyl, alkoxycarbonylamino, alkylcarbonylamino or alkoxycarbonyl;

$R_2$ is alkyl, haloalkyl, alkoxy, haloalkoxy or unsubstituted or substituted phenyl;

$R_3$ is hydrogen, halogen, nitro, amino, alkylamino, haloalkylamino, cyano or amide;

$R_4$ and $R_5$ are independently oxygen, sulfur or imino; Q6, Q7, Q10, Q16 or Q17 may be unsaturated containing one or two double bonds in the 6-membered ring;

R is hydrogen, alkyl, alkenyl, alkynyl, cycloalkyl, cycloalkylalkyl, alkoxyalkyl, alkoxyalkoxyalkyl, alkylcarbonyl, arylcarbonyl, alkoxycarbonyl, aryloxycarbonyl, alkoxycarbonylalkyl, alkoxyalkoxycarbonylalkyl, cycloalkoxycarbonylalkyl, aralkyl, heteroaralkyl, aryloxyalkyl or heteroaryloxyalkyl where any of these groups may be substituted with at least one substituent selected from the group consisting of halogen, cyano, nitro, amino, carboxyl, alkylthioalkyl, hydroxyalkyl, $CON(R_6)R_7$ and $COON(R_6)R_7$;

$R_6$ and $R_7$ are independently hydrogen, halogen, alkyl, alkenyl, alkynyl, cycloalkyl, alkoxyalkyl, alkylthioalkyl, alkoxycarbonylalkyl, cycloalkoxycarbonylalkyl, alkylcarbonyloxyalkyl, alkylcarbonylaminoalkyl, alkoxyalkylcarbonylalkyl, phenyl or benzyl where any of these groups may be substituted with at least one substituent selected from the group consisting of halogen, cyano, carboxyl, hydroxy, nitro and amino;

W is O, S or imino;

n is an integer of 0 or 1;

—L—X— is —O—, —S—, —CR$_8$R$_9$—, —CR$_8$R$_9$—O—, —CR$_8$R$_9$—S—, —CR$_8$R$_9$—CR$_8$R$_9$—, —CR$_8$=CR$_9$—, —CR$_8$=N—, —N=CR$_9$— or —N=N—;

R$_8$ and R$_9$ are independently hydrogen, halogen, alkyl, alkenyl, alkynyl, cycloalkyl, alkoxyalkyl, alkylthioalkyl, alkoxycarbonylalkyl, cycloalkoxycarbonylalkyl, alkylcarbonyloxyalkyl, alkylcarbonylaminoalkyl, alkoxyalkylcarbonylalkyl, phenyl or benzyl where any of these groups may be substituted with at least one substituent selected from the group consisting of halogen, cyano, carboxyl, hydroxy, nitro and amino;

Y is hydrogen or halogen;

Z is nitro, isocyanate, amino, hydroxyl, thiol, formyl, carboxyl, cyano, halogen, unsubstituted or substituted alkyl, alkenyl, alkylcarbonyl, arylcarbonyl, azido or one of the following:

wherein R$_{10}$ is alkyl, alkenyl, alkynyl, amino, cycloalkyl, heterocycloalkyl, alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heteroarylcarbonyl, alkoxycarbonyl, alkylthiocarbonyl, cycloalkyloxycarbonyl, aryloxycarbonyl, arylthio-carbonyl, arylthiocarbonyl, heteroaryloxycarbonyl, aminocarbonyl, alkylaminocarbonyl, arylaminocarbonyl, heteroarylaminocarbonyl, alkoxycarbonylcarbonyl or arylcarbonylcarbonyl where any of these groups may be substituted with at least one substituent selected from the group consisting of halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl and methylenedioxy, wherein the alkyl moiety or aryl moiety may be substituted with at least one substituent selected from the group consisting of halogen, cyano, nitro, alkyl, alkoxy, haloalkyl, haloalkoxy, alkoxycarbonyl, cycloalkyl, aryl and heterocycloalkyl;

R$_{11}$ is hydrogen or any one of the groups represented by R$_{10}$;

R$_{10}$ and R$_{11}$ may combine to form a 4–8 membered heterocyclic ring;

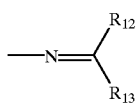

wherein R$_{12}$ is alkyl, haloalkyl, dialkylamino, unsubstituted or substituted aryl or heteroaryl;

R$_{13}$ is hydrogen, halogen or any of the groups represented by R$_{12}$;

—OR$_{10}$, —SR$_{10}$, —CH$_2$R$_{14}$, —CH(R$_{14}$)$_2$, —C(R$_{14}$)$_3$ or —CH=CHR$_{14}$ wherein R$_{14}$ is carboxyl, alkyl, alkenyl, alkynyl, amino, cycloalkyl, heterocycloalkyl, alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heterocrylcarbonyl, alkoxycarbonyl, alkylthiocarbonyl, cycloalkyloxycarbonyl, aryloxycarbonyl, arylthio-carbonyl, arylthiocarbonyl, heteroaryloxycarbonyl, aminocarbonyl, alkylaminocarbonyl, arylaminocarbonyl, heteroarylaminocarbonyl, alkoxycarbonylcarbonyl, or arylcarbonylcarbonyl where any of these groups may be substituted with at least one substituent selected from the group consisting of halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkythiocarbonyl, alkoxythiocarbonyl, alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl and methylenedioxy, wherein the alkyl moiety or aryl moiety may be substituted with at least one substituent selected from the group consisting of halogen, cyano, nitro, alkyl, alkoxy, haloalkyl, haloalkoxy, alkoxycarbonyl, cycloalkyl, aryl and heterocycloalkyl;

provided that
(1) Z is not nitro or amino when Q is Q3 and R$_2$ is haloalkyl; and
(2) Z is not amino or

wherein R$_{10}$ is alkyl, alkenyl or alkynyl, and R$_{11}$ is hydrogen, alkyl, alkenyl or alkynyl, when Q is Q20.

DETAILED DESCRIPTION OF THE INVENTION

In the above definitions, the term alkyl used either alone or in compound words such as haloalkyl or alkoxy indicates either straight chain or branched alkyls containing 1–8 carbon atoms. Alkenyl and alkynyl include straight chain or branched alkenes and alkynes respectively containing 2–8 carbon atoms. The term halogen either alone or in the compound words such as haloalkyl indicates fluorine, chlorine, bromine, or iodine. Further a haloalkyl is represented by an alkyl partially or fully substituted with halogen atoms that may be same or different. A cycloalkyl group implies a saturated or unsaturated carbocycle containing 3–8 carbon atoms. A heterocycloalkyl group is a cycloalkyl group carrying 1–4 heteroatoms which are representd by oxygen, nitrogen, or sulfur atoms. An aryl group signifies an aromatic carbocycle containing 4–10 carbon atoms. A heteroaryl group is an aromatic ring containing 1–4 heteroatoms which are represented by oxygen, nitrogen, or sulfur atoms, and may for example be furanyl, pyridyl, thienyl, pyrimidinyl, benzofuranyl, quinolyl, benzothienyl or quinoxalyl.

The compound of the formula (I) may form a salt with an acidic substance or a basic substance. The salt with an acidic substance may be an inorganic acid salt such as a hydrochloride, a hydrobromide, a phosphate, a sulfate or a nitrate. The salt with a basic substance may be a salt of an inorganic or organic base such as a sodium salt, a potassium salt, a calcium salt, a quarternary ammonium salt such as ammonium salt or a dimethylamine salt.

The compound of the formula (I) may exist as geometrical or optical isomers and the present invention includes all of these isomeric forms.

Preferred compounds for the reasons of ease of synthesis or greater herbicidal efficacy are represented by the formula (I) wherein;

(1) the formula (I) is

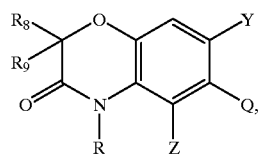  I-1

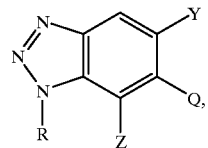  I-2

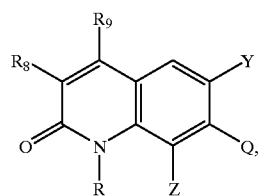  I-3

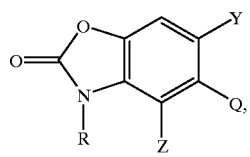  I-4

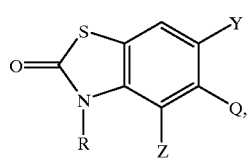  I-5

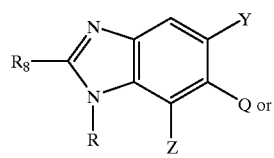  I-6

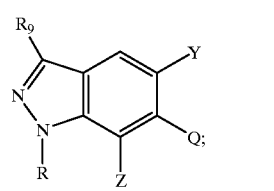  I-7

Wherein Q, R, $R_8$, $R_9$ and Y are the same as defined above;

(2) Q is Q1–5, Q16 or Q17;

(3) Y is fluorine;

More preferred is a compound of the formula (I-1)

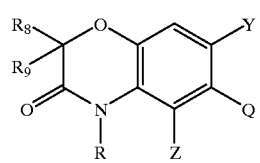  I-1

Wherein Q is Q1; Y is fluorine; and R, $R_8$, $R_9$ and Z are the same as defined in claim 1.

Specific examples of preferred compounds are as follows: 3-[5-amino-7-fluoro-2H-1,4-benzoxazine-3(4H)-on-6-yl]-1-methyl-6-trifluoromethyl-2,4-(1H,3H)-pyrimidinedione, 3-[5-(2-naphthoyl)amino-7-fluoro-2H-1,4-benzoxazine-3(4H)-on-6-yl]-1-methyl-6-trifluoromethyl-2,4-(1H,3H)-pyrimidinedione or 3-[5-cinnamoylamino-7-fluoro-2H-1,4-benzoxazine-3(4H)-on-6-yl]-1-methyl-6-trifluoromethyl-2,4-(1H,3H)-pyrimidinedione.

The compound of the formula (I) can be produced, for example, by the following metods A to C:

A

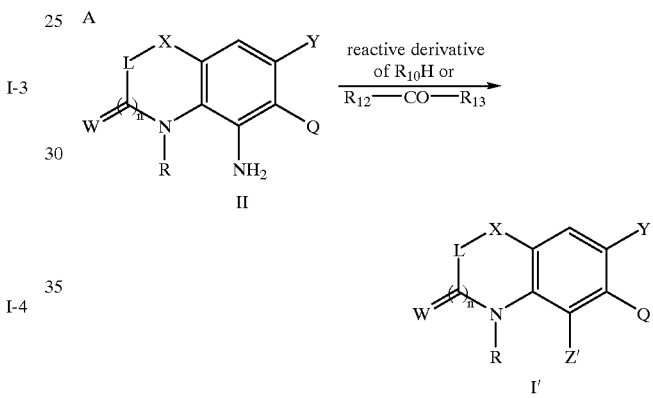

In the above formulas, Q, R, W, —L—X—, Y, n, $R_{10}$, $R_{12}$ and $R_{13}$, are the same as defined above and Z' is —$NR_{10}R_{11}$ or —N=$CR_{12}R_{13}$.

The reactive derivative of $R_{10}H$ or $R_{12}$—CO—$R_{13}$ may, for example, be a compound selected from the group consisting of an alkyl halide, alkyl acid halide, aryl acid halide, alkyl acid anhydride, aryl acid anhydride, alkylhaloformate, alkyl isocyanate, aryl isocyanate, alkyl dihalide, aliphatic aldehyde, aliphatic ketone, aromatic aldehyde, and aromatic ketone.

The reaction is conducted usually in the presence of a solvent, if necessary, in the presence of a base. The solvent may, for example, be an aromatic hydrocarbon such as benzene or toluene; an ether such as diethyl ether, tetrahydrofuran or dioxane; a halogenated hydrocarbon such as methylene chloride or chloroform; an aprotic polar solvent such as acetonitrile, dimethylformamide or pyridine. The base may, for example, be a tertiary amine such as trimethylamine, triethylamine; a pyridine; an alkali metal hydroxide such as sodium hydroxide or potassium hydroxide; an alkali metal carbonate such as sodium carbonate or potassium carbonate; or an alkali metal alkoxide such as sodium methoxide or sodium ethoxide.

The reaction temperature is usually from −50° to +150° C., preferably from 0° to 100° C. The reaction time is form 0.1 to 24 hours.

B

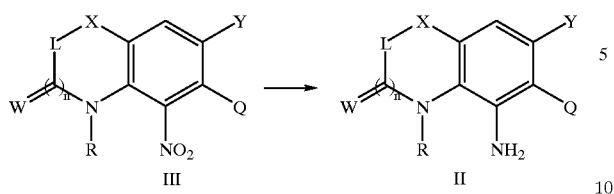

In the above formulas, Q, R, W, —L—X—, Y and n are the same as defined above.

The above reaction is carried out by treatment with iron in acetic acid or ethanolic hydrochloric acid, or by hydrogenation using palladium on carbon or platinum oxide as catalyst.

The reaction temperature is usually from 0° to 50° C. The reaction time is form 0.1 to 24 hours.

The above reaction is carried out in nitric acid or fuming nitric acid which may be mixed with sulfuric acid or acetic acid. The amount of nitric acid is usually from 1 to 100 moles per one mole of the compound of the formula IV.

The reaction temperature is usually from 0° to 100° C. The reaction time is form 0.1 to 24 hours.

The compound of the formula (I) can also be prepared by the procedures as described herein.

SCHEME 1

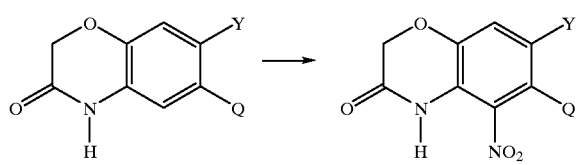

SCHEME 2

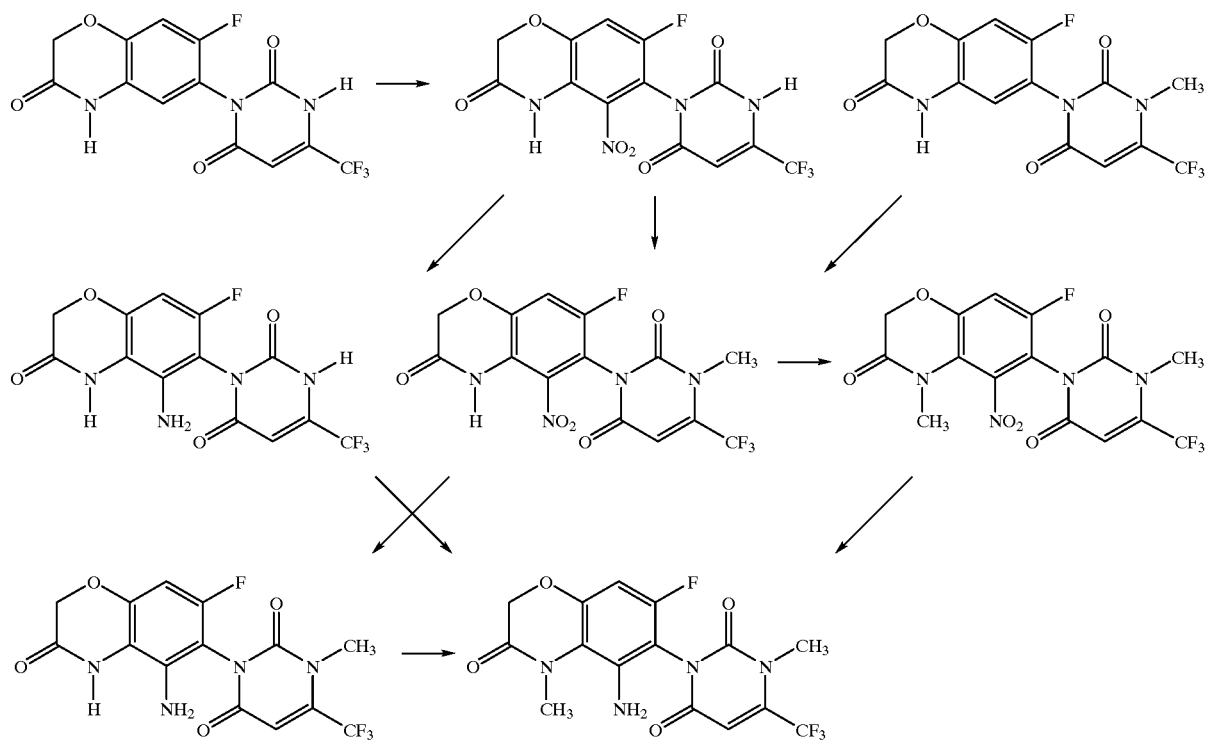

C

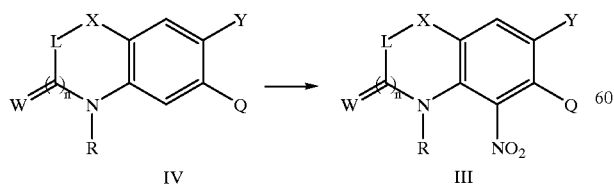

In the above formulas, Q, R, W, —L—X—, Y and n are the same as defined above.

SCHEME 3

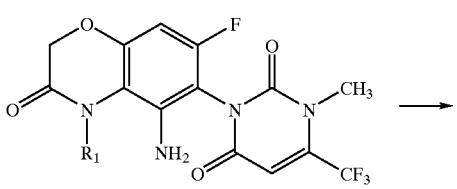

-continued
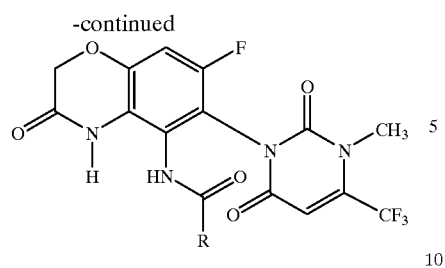
SCHEME 4
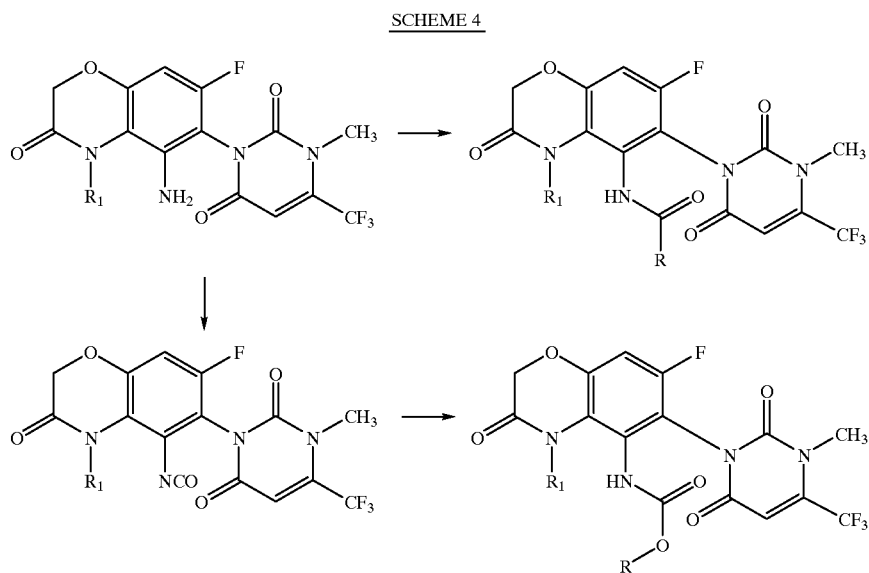
SCHEME 5
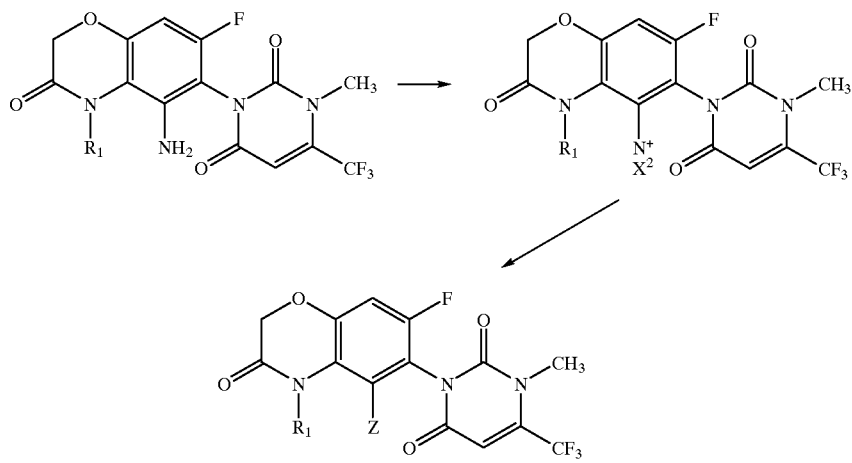

SCHEME 6
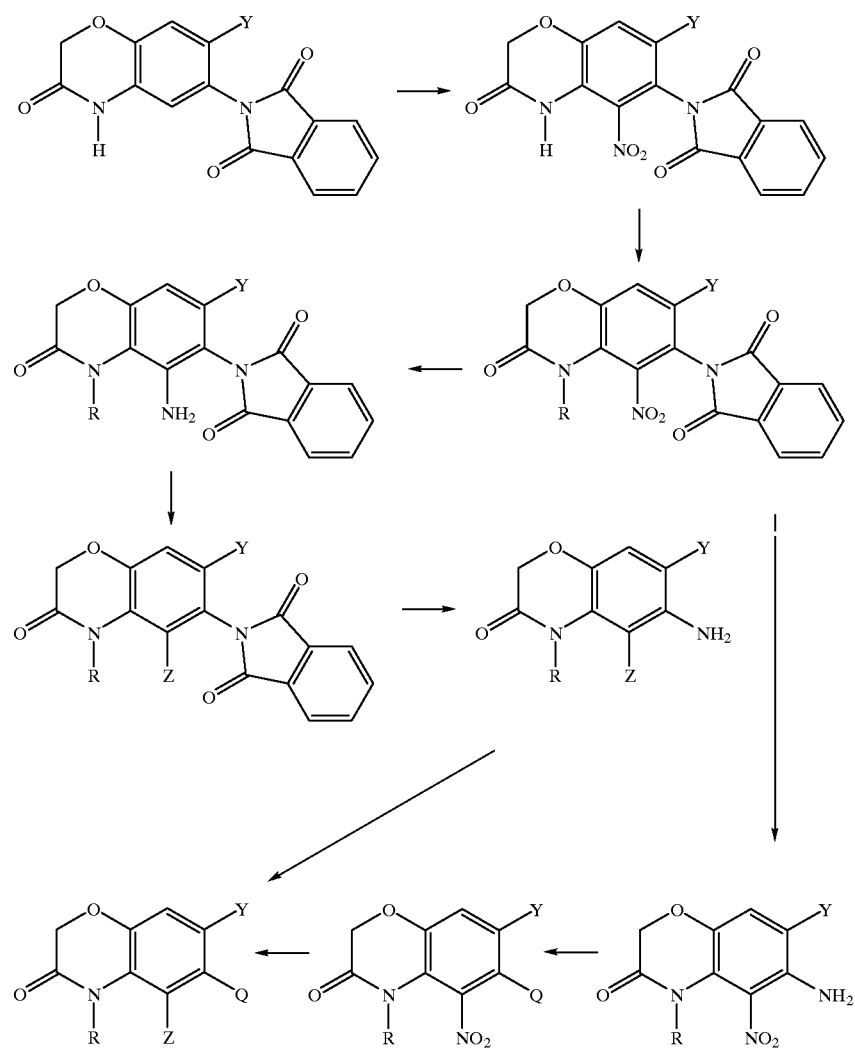

SCHEME 7
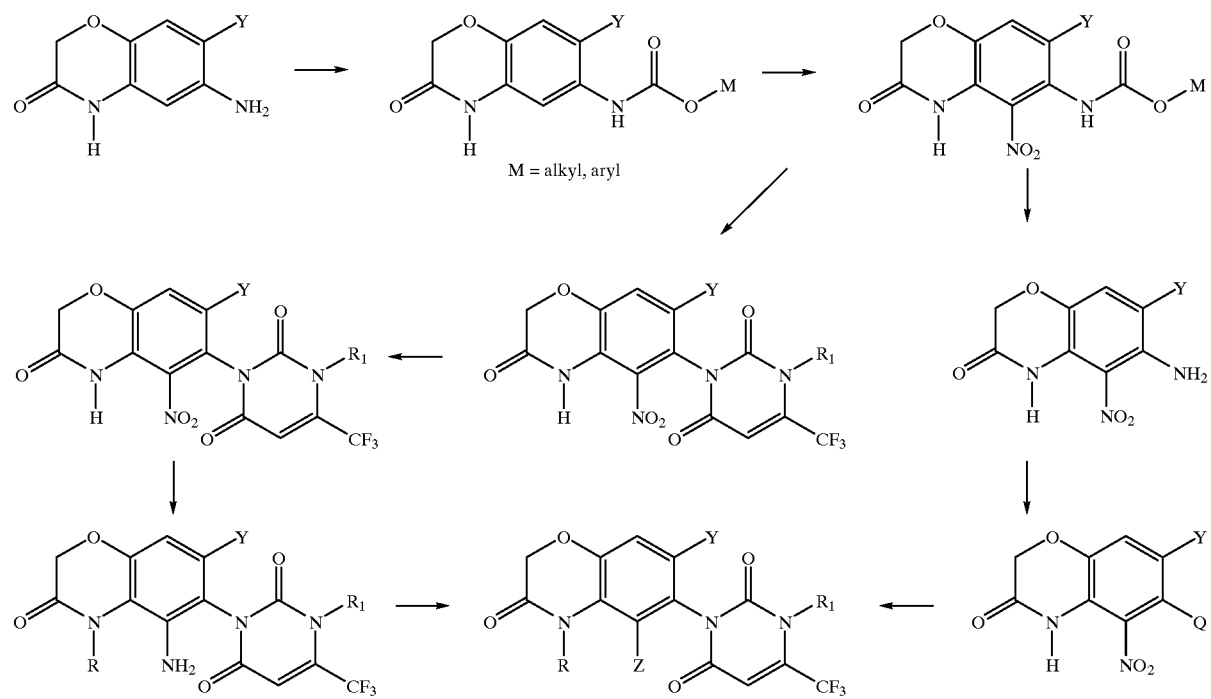

SCHEME 8

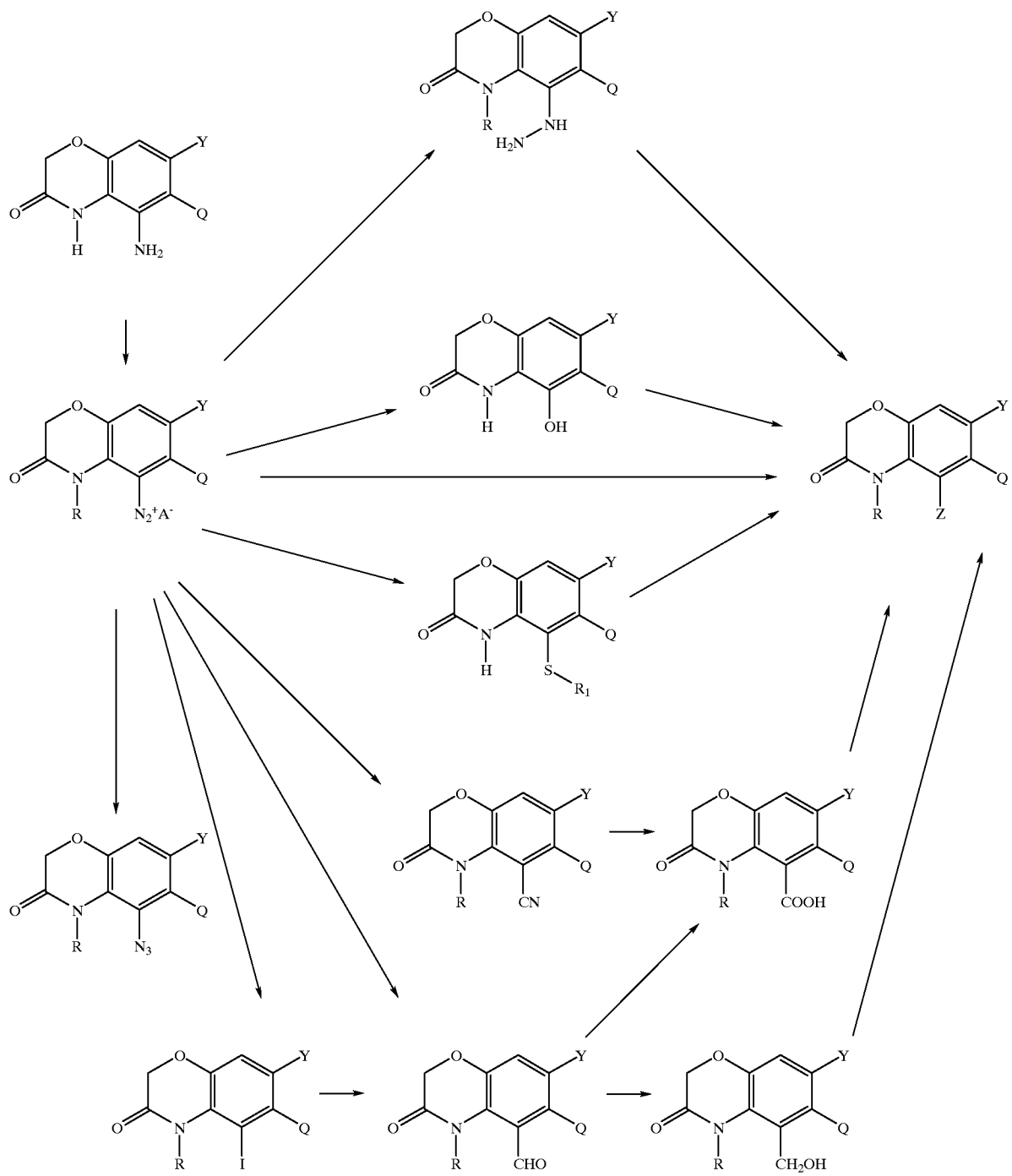

Now, the present invention will be described with reference to Examples. However, it should be understood that the present invention is by no means restricted by these specific Examples.

EXAMPLE 1
Preparation of 3-[7-fluoro-5-nitro-2H-1,4-benzoxazine-3(4H)-on-6-yl]-6-trifluoromethyl-2,4-(1H, 3H)-pyrimidinedione (Compound No.1-1).
3-[7-Fluoro-2H-1,4-benzoxazine-3(4H)-on-6-yl]-6-trifluoromethyl-2,4-(1H, 3H)-pyrimidinedione (7.0 g) was added by portion to a mixture of acetic acid (30 ml) and fuming nitric acid (90 ml) at 0° C. After stirring for 1 hr at room temperature, the solution was mixed with ice-water (200 ml) and then extracted with ethyl acetate (60 ml×3). The organic layers were combined and washed with water (20 ml×2) and brine (20 ml), dried over sodium sulfate. After filtration and evaporation, the residue was recrystallized from methylene chloride (8.3 g).

EXAMPLE 2
Preparation of 3-[7-fluoro-4-methyl-5-nitro-2H-1,4-benzoxazine-3(4H)-on-6-yl]-1-methyl-6-trifluoromethyl-2,4-(1H,3H)-pyrimidinedione (Compound No.1-2).

3-[7-Fluoro-5-nitro-2H-1,4-benzoxazine-3(4H)-on-6-yl]-6-trifluoromethyl-2,4-(1H, 3H)-pyrimidinedione (1.0 g) was dissolved in DMF (20 ml) containing potassium carbonate (1.0 g) and iodomethane (0.5 ml). The mixture was stirred for 2 hr and then water (30 ml) and ethyl acetate (40 ml) were added. The organic phase was washed with water (15 ml×2) and brine (15 ml), then dried over sodium sulfate. Filtration and evaporation gave the title compound (0.9 g).

EXAMPLE 3
Preparation of 3-[5-amino-7-fluoro-4-methyl-2H-1,4-benzoxazine-3(4H)-on-6-yl]-1-methyl-6-trifluoromethyl-2,4-(1H,3H)-pyrimidinedione (Compound No.1-4)

3-[7-Fluoro-4-methyl-5-nitro-2H-1,4-benzoxazine-3(4H)-on-6-yl]-1-methyl-6-trifluoromethyl-2,4-(1H, 3H)-pyrimidinedione (1.45 g) was dissolved in acetic acid (80 ml) containing iron powder (1.16 g). The mixture was stirred for 3 days under nitrogen atmosphere. After filtration, water (100 ml) and ethyl acetate (150 ml) were added to the filtrate, the organic phase was washed with water (30 ml×3) and brine (30 ml), dried over sodium sulfate. After filtration and evaporation, the residue was purified by silica gel column (hexane to 40% ethyl acetate) to afford the title compound (1.1 g).

EXAMPLE 4
Preparation of 3-[5-amino-7-fluoro-2H-1,4-benzoxazine-3(4H)-on-6-yl]-1-methyl-6-trifluoromethyl-2,4-(1H,3H)-pyrimidinedione (Compound No.1-6)

3-[5-Amino-7-fluoro-2H-1,4-benzoxazine-3(4H)-on-6-yl]-6-trifluoromethyl-2,4-(1H, 3H)-pyrimidinedione (4.0 g) was dissolved in DMF (200 ml) containing potassium carbonate (5 g) and iodomethane (10 ml). After stirring for 2 hr, water (150 ml) and ethyl acetate (200 ml) were added. The organic phase was washed with water (50 ml×3) and brine (50 ml), dried over sodium sulfate. After filtration and evaporation, the residue was recrystallized from methylene chloride and hexane to afford the title compound (3.3 g).

EXAMPLE 5
Preparation of 3-[5-(2-naphthoyl)amino-7-fluoro-4-methyl-2H-1,4-benzoxazine-3(4H)-on-6-yl]-1-methyl-6-trifluoromethyl-2,4-(1H, 3H)-pyrimidinedione (Compound No.1-12)

3-[5-Amino-7-fluoro-4-methyl-2H-1,4-benzoxazine-3(4H)-on-6-yl]-1-methyl-6-trifluoromethyl-2,4-(1H, 3H)-pyrimidinedione (0.49 g) and 2-naphthoyl chloride (0.26 g) were mixed in dioxane (35 ml), the resulting mixture was refluxed for 7 hr. After evaporation, the residue was purified by silica gel column (hexane to 30% and 50% ethyl acetate) to yield the title compound (0.3 g).

EXAMPLE 6
Preparation of 3-[5-(2-naphthoyl)amino-7-fluoro-2H-1,4-benzoxazine-3(4H)-on-6-yl]-1-methyl-6-trifluoromethyl-2,4-(1H,3H)-pyrimidinedione (Compound No.1-13)

3-[5-Amino-7-fluoro-2H-1,4-benzoxazine-3(4H)-on-6-yl]-1-methyl-6-trifluoromethyl-2,4-(1H, 3H)-pyrimidinedione (0.37 g) and 2-naphthoyl chloride (0.21 g) were mixed in dioxane (15 ml) and the mixture was refluxed for 6 hr. After evaporation of solvent, the residue was recrystallized from toluene (0.20 g).

EXAMPLE 7
Preparation of 3-[7-fluoro-4-methyl-5-(3-nitrobenzyloxycarbonyl)-amino-2H-1,4-benzoxazine-3(4H)-on-6-yl]-1-methyl-6-trifluoromethyl-2,4-(1H, 3H)-pyrimidinedione (Compound No. 1-22)

3-[5-Amino-7-fluoro-4-methyl-2H-1,4-benzoxazine-3(4H)-on-6-yl]-1-methyl-6-trifluoromethyl-2,4-(1H, 3H)-pyrimidinedione (0.42 g) was mixed with triphosgene (0.32 g) and triethylamine (0.22 g) in toluene (80 ml) and the resulting mixture refluxed for 20 hr. After filtration and evaporation, the residue was mixed with 3-nitrobenzyl alcohol (0.16 g) and triethylamine (0.11 g) in toluene (15 ml) and the mixture stirred for 2 hr. After evaporation of solvent, the residue was purified by silica gel column (hexane to 60% ethyl acetate) to afford the title compound (0.22 g).

EXAMPLE 8
Preparation of 3-[5-(2-chloro-3-ethoxycarbonyl-1-propyl)-7-fluoro-4-methyl-2H-1,4-benzoxazine-3(4H)-on-6-yl]-1-methyl-6-trifluoromethyl-2,4-(1H, 3H)-pyrimidinedione (Compound No.1-14)

3-[5-Amino-7-fluoro-4-methyl-2H-1,4-benzoxazine-3(4H)-on-6-yl]-1-methyl-6-trifluoromethyl-2,4-(1H, 3H)-pyrimidinedione (0.78 g) was mixed with acetonitrile (4 ml), the mixture was slowly added into a flask of −60° C. containing ethyl acrylate (10 ml), acetonitrile (3 ml), $CuCl_2$ (0.35 g) and tert-butylnitrite (0.4 ml). After stirring for 1 hr, the cooling bath was removed and reaction continued for 15 hr. Water (15 ml) and methylene chloride (30 ml) were added and the heavier phase was washed with water (20 ml×3) and then dried over sodium sulfate. After filtration and evaporation, the residue was purified by column chromatography (silica gel, hexane to 25% ethyl acetate) to yield the title compound (0.2 g) as a diastereomeric mixture.

EXAMPLE 9
Preparation of 2-[7-fluoro-5-nitro-2H-1,4-benzoxazine-3(4H)-on-6-yl]-4,5,6,7-tetrahydro-2H-isoindole-1,3-dione (Compound No.2-1)

2-[7-Fluoro-2H-1,4-benzoxazine-3(4H)-on-6-yl]-4,5,6,7-tetrahydro-2H-isoindole-1,3-dione (1.0 g) was stirred in acetic acid (20 ml) and fuming nitric acid (8 ml) was slowly added. Solution was stirred at ambient temperature for 1 hr and the clear solution was added to ice-water. Light yellow precipitate was separated by filtration to afford the title compound (0.95 g).

EXAMPLE 10
Preparation of 2-[5-amino-7-fluoro-2H-1,4-benzoxazine-3(4H)-on-6-yl]-4,5,6,7-tetrahydro-2H-isoindole-1,3-dione (Compound No.2-2)

2-[7-Fluoro-5-nitro-2H-1,4-benzoxazine-3(4H)-on-6-yl]-4,5,6,7-tetrahydro-2H-isoindole-1,3-dione (1.25 g) was dissolved in acetic acid (13 ml) and iron powder (0.77 g) was added with stirring. Solution was stirred at ambient temperature for 12 hr and water was added. Product was extracted with ethyl acetate to afford the title compound (1.2 g).

EXAMPLE 11
Preparation of 2-[7-fluoro-4-methyl-5-nitro-2H-1,4-benzoxazine-3(4H)-on-6-yl]-4,5,6,7-tetrahydro-2H-isoindole-1,3-dione (Compound No.2-3)

2-[7-Fluoro-5-nitro-2H-1,4-benzoxazine-3(4H)-on-6-yl]-4,5,6,7-tetrahydro-2H-isoindole-1,3-dione (1.3 g) was dissolved in anhydrous dimethylformamide (15 ml) and was slowly added to a stirred suspension of sodium hydride (0.11 g) in dimethylformamide (15 ml) under ice cooling. Solution was stirred for 0.5 hr followed by the addition of methyl iodide (2.03 g). After stirring for 2 hr at ambient temperature, solution was added to ice-water and product was isolated by partitioning with ethyl acetate. Purification by column chromatography on silica gel in hexane-ethyl acetate (3:1) afforded the title compound (0.58 g).

EXAMPLE 12
Preparation of 2-[5-amino-7-fluoro-4-methyl-2H-1,4-benzoxazine-3(4H)-on-6-yl]-4,5,6,7-tetrahydro-2H-isoindole-1,3-dione (Compound No.2-4)

2-[7-Fluoro-4-methyl-5-nitro-2H-1,4-benzoxazine-3 (4H)-on-6-yl]-4,5,6,7-2o tetrahydro-2H-isoindole-1,3-dione (0.58 g) was dissolved in acetic acid (6 ml) and iron powder (0.35 g) was added followed by stirring at ambient temperature for 12 hr. Water was added and product isolated by partitioning with ethyl acetate to afford the title compound (0.54 g).

EXAMPLE 13
Preparation of 2-[5-(2-naphthoyl)amino-7-fluoro-4-methyl-2H-1,4-benzoxazine-3(4H)-on-6-yl]-4,5,6,7-tetrahydro-2H-isoindole-1,3-dione (Compound No.2-5)

2-[5-Amino-7-fluoro-4-methyl-2H-1,4-benzoxazine-3 (4H)-on-6-yl]-4,5,6,7-tetrahydro-2H-isoindole-1,3-dione (0.3 g) and 2-naphthoyl chloride (0.19 g) were dissolved in anhydrous dioxane (10 ml) and the solution refluxed for 2 hr. Solvent was evaporated and the residue subjected to column chromatography on silica gel in hexane-ethyl acetate (6:4) to furnish the title compound (0.15 g).

EXAMPLE 14
Preparation of 2-[7-fluoro-5-nitro-2H-1,4-benzoxazin-3 (4H)-on-6-yl]-4-difluoromethyl-3-methyl-1,4-dihydro-1,2,4-triazin-5-one (Compound No.3-1)

2-[7-Fluoro-2H-1,4-benzoxazine-3(4H)-on-6-yl]-4-difluoromethyl-3-methyl-1,4-dihydro-1,2,4-triazin-5-one (0.38 g) was dissolved in acetic acid (10 ml) and fuming nitric acid (10 ml) was added slowly at ambient temperature. The resulting mixture was stirred for 1 hour and poured into ice-water. The mixture was extracted with ethyl acetate, washed with brine and dried over anhydrous sodium sulfate. The solvent was removed in vacuo and the residue was purified by column chromatography on silica gel eluted with ethyl acetate and hexanes (1:3) to give title compound (0.17 g).

EXAMPLE 15
Preparation of 2-[7-fluoro-5-nitro-2H-1,4-benzoxazine-3 (4H)-on-6-yl]-(4-fluoropropyl)-1,4-dihydro-5-oxo-5H-tetrazole (Compound No.4-1)

2-[7-Fluoro-2H-1,4-benzoxazine-3(4H)-on-6-yl]-(4-fluoropropyl)-1,4-dihydro-5-oxo-5H-tetrazole (4.15 g) was stirred in acetic acid (40 ml) and fuming nitric acid (20 ml) was slowly added. Solution was stirred at ambient temperature for 3 hr and the clear solution was added to ice-water Light yellow precipitate was separated by filtration to afford the title compound (3.42 g).

EXAMPLE 16
Preparation of 2-[5-amino-7-fluoro-2H-1,4-benzoxazine-3 (4H)-on-6-yl]-(4-fluoropropyl)-1,4-dihydro-5-oxo-5H-tetrazole (Compound No.4-2)

2-[7-Fluoro-5-nitro-2H-1,4-benzoxazine-3(4H)-on-6-yl]-(4-fluoropropyl)-1,4-dihydro-5-oxo-5H-tetrazole (1.069 g) was dissolved in acetic acid (20 ml) and iron powder (0.838 g) was added with stirring. Solution was stirred at ambient temperature overnight. The reaction mixture was partitioned between water and ethyl acetate. The ethyl acetate phase was concentrated. The crystals appeared were collected by filtration to afford the title compound (0.808 g).

EXAMPLE 17
Preparation of 2-[7-fluoro-4-methyl-5-nitro-2H-1,4-benzoxazine-3(4H)-on-6-yl]-(4-fluoropropyl)-1,4-dihydro-5-oxo-5H-tetrazole (Compound No.4-3)

A mixture of 2-[7-fluoro-5-nitro-2H-1,4-benzoxazine-3 (4H)-on-6-yl]-(4-fluoropropyl)-1,4-dihydro-5-oxo-5H-tetrazole (1.069 g), methyl iodide (0.85 g), and potassium carbonate (0.5 g) was stirred for 3 hrs at ambient temperature. The reaction mixture was partitioned between water and ethyl acetate. The ethyl acetate phase was evaporated to give the title compound (1.14 g, oil).

EXAMPLE 18
Preparation of 2-[5-amino-7-fluoro-4-methyl-2H-1,4-benzoxazine-3(4H)-on-6-yl]-(4-fluoropropyl)-1,4-dihydro-5-oxo-5H-tetrazole (Compound No.4-5)

2-[7-fluoro-4-methyl-5-nitro-2H-1,4-benzoxazine-3(4H)-on-6-yl]-(4-fluoropropyl)-1,4-dihydro-5-oxo-5H-tetrazole (1.1 g) was dissolved in acetic acid (20 ml) and iron powder (0.829 g) was added and stirred at ambient temperature overnight. The reaction mixture was partitioned between water and ethyl acetate. The ethyl acetate phase was evaporated to give the title compound (0.80 g, amorphous).

EXAMPLE 19
Preparation of 3-[7-fluoro-5-nitro-2H-1,4-benzoxazine-3 (4H)-on-6-yl]-1-methyl-6-trifluoromethyl-2,4-(1H, 3H)-pyrimidinedione (Compound No.1-24)

3-[7-Fluoro-2H-1,4-benzoxazine-3(4H)-on-6-yl]-1-methyl-6-trifluoromethyl-2,4-(1H, 3H)-pyrimidinedione (3.5 g) was slowly added to a mixture of acetic acid (15 ml) and fuming nitric acid (45 ml) at 0° C. with stirring. After stirring for 2 hr at room temperature, the solution was poured on ice-water and extracted with ethyl acetate. The organic layer was washed with water and brine, dried over sodium sulfate and evaporated. The residue was purified by column chromatography on silica gel using hexane-ethyl acetate (6:4) as eluent to afford the title compound (3.25 g).

Using the procedures as described in Schemes 1–8 and Examples 1–18, the compounds of this invention can be readily prepared. Tables 1–7 list structures for few representative examples of this invention.

TABLE 1
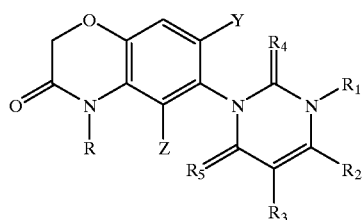
| No. | Y | R₁ | R₂ | R₃ | R₄ | R₅ | R | Z |
|---|---|---|---|---|---|---|---|---|
| 1-1 | F | H | CF₃ | H | O | O | H | NO₂ |
| 1-2 | F | CH₃ | CF₃ | H | O | O | CH₃ | NO₂ |
| 1-3 | F | H | CF₃ | H | O | O | H | NH₂ |
| 1-4 | F | CH₃ | CF₃ | H | O | O | CH₃ | NH₂ |
| 1-5 | F | CH₃ | CF₃ | H | O | O | CH₃ | NHOH |
| 1-6 | F | CH₃ | CF₃ | H | O | O | H | NH₂ |
| 1-7 | F | CH₃ | CF₃ | H | O | O | CH₂CCH | NH₂ |
| 1-8 | F | CH₃ | CF₃ | H | O | O | CH₃ | NHCH₃ |
| 1-9 | F | CH₃ | CF₃ | H | O | O | CH₃ | Cl |
| 1-10 | F | CH₃ | CF₃ | H | O | O | H | NHCOC(CH₃)₃ |
| 1-11 | F | CH₃ | CF₃ | H | O | O | CO₂CH₂CH₃ | NH₂ |
| 1-12 | F | CH₃ | CF₃ | H | O | O | CH₃ | 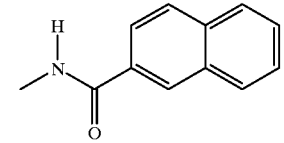 |
| 1-13 | F | CH₃ | CF₃ | H | O | O | H | 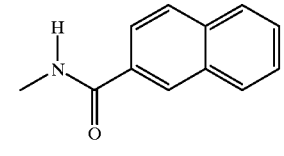 |
| 1-14 | F | CH₃ | CF₃ | H | O | O | H | 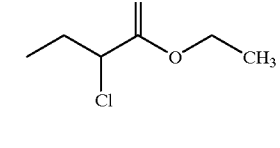 |
| 1-15 | F | CH₃ | CF₃ | H | O | O | 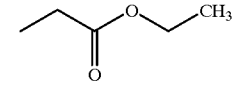 | 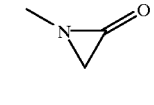 |
| 1-16 | F | CH₃ | CF₃ | H | O | O | H | 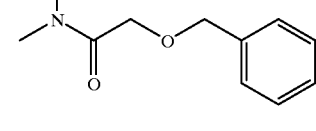 |
| 1-17 | F | CH₃ | CF₃ | H | O | O | H | 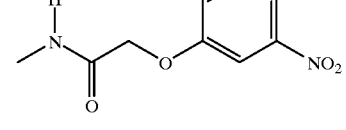 |
| 1-18 | F | CH₃ | CF₃ | H | O | O | H | 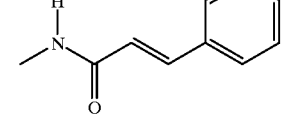 |

TABLE 1-continued

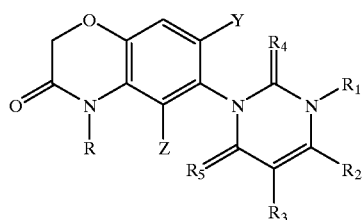

| No. | Y | $R_1$ | $R_2$ | $R_3$ | $R_4$ | $R_5$ | R | Z |
|---|---|---|---|---|---|---|---|---|
| 1-19 | F | $CH_3$ | $CF_3$ | H | O | O | H | 2,4-difluoro-N-methylbenzamide |
| 1-20 | F | $CH_3$ | $CF_3$ | H | O | O | $CH_3$ | —NCO |
| 1-21 | F | $CH_3$ | $CF_3$ | H | O | O | $CH_3$ | phenyl N-methylcarbamate |
| 1-22 | F | $CH_3$ | $CF_3$ | H | O | O | $CH_3$ | (3-nitrobenzyl) N-methylcarbamate |
| 1-23 | F | $CH_3$ | $CF_3$ | H | O | O | $CH_3$ | N-methyl-N-(cyclopropanecarbonyl)cyclopropanecarboxamide |
| 1-24 | F | $CH_3$ | $CF_3$ | H | O | O | H | $NO_2$ |
| 1-25 | F | $CH_3$ | $CF_3$ | H | O | O | H | N-methylquinoxaline-2-carboxamide |
| 1-26 | F | $CH_3$ | $CF_3$ | H | O | O | $CH_3$ | N-methylquinoxaline-2-carboxamide |
| 1-27 | F | $CH_3$ | $CF_3$ | H | O | O | H | N-methyl-4-vinylbenzamide |

TABLE 1-continued
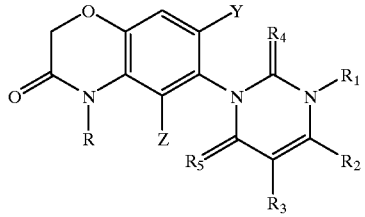
| No. | Y | R₁ | R₂ | R₃ | R₄ | R₅ | R | Z |
|-----|---|-----|-----|----|----|----|---|---|
| 1-28 | F | CH₃ | CF₃ | H | O | O | CH₃ | 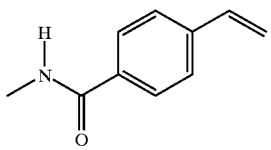 |
| 1-29 | F | CH₃ | CF₃ | H | O | O | H | 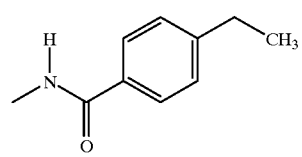 |
| 1-30 | F | CH₃ | CF₃ | H | O | O | CH₃ | 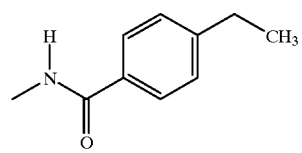 |
| 1-31 | F | CH₃ | CF₃ | H | O | O | H | 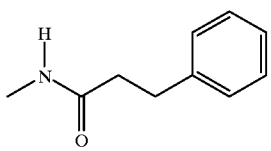 |
| 1-32 | F | CH₃ | CF₃ | H | O | O | CH₃ | 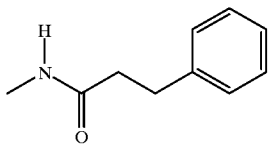 |
| 1-33 | F | CH₃ | CF₃ | H | O | O | CH₃ | 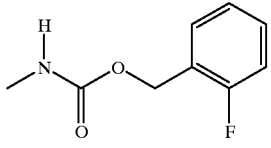 |
| 1-34 | F | CH₃ | CF₃ | H | O | O | CH₃ | 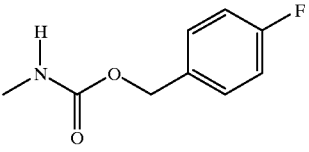 |
| 1-35 | Cl | CH₃ | CF₃ | H | O | O | H | 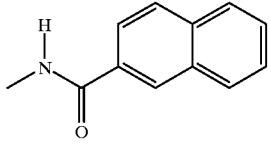 |

TABLE 1-continued
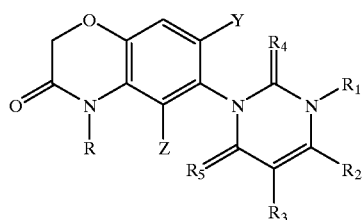
| No. | Y | R₁ | R₂ | R₃ | R₄ | R₅ | R | Z |
|---|---|---|---|---|---|---|---|---|
| 1-36 | F | CH₃ | CF₃ | H | S | O | H | 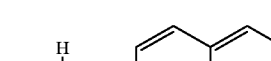 |
| 1-37 | F | CH₃ | CF₃ | H | O | S | H |  |
TABLE 2
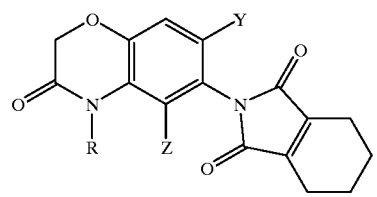
| No. | Y | R | Z |
|---|---|---|---|
| 2-1 | F | H | NO₂ |
| 2-2 | F | H | NH₂ |
| 2-3 | F | CH₃ | NO₂ |
| 2-4 | F | CH₃ | NH₂ |
| 2-5 | F | CH₃ | 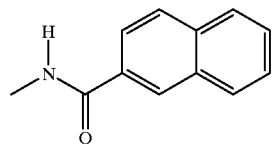 |
| 2-6 | F | CH₃ | 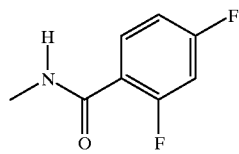 |
| 2-7 | F | H | 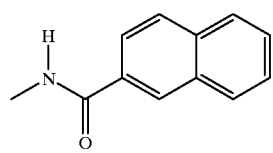 |
TABLE 2-continued
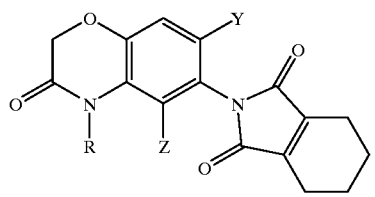
| No. | Y | R | Z |
|---|---|---|---|
| 2-8 | F | CH₃ | 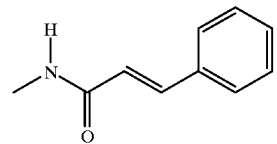 |
| 2-9 | F | CH₃ | 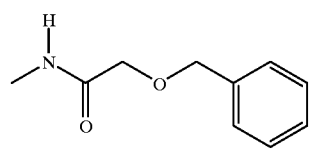 |
| 2-10 | F | CH₃ | 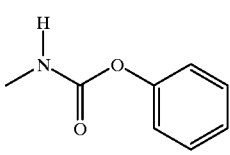 |

TABLE 2-continued

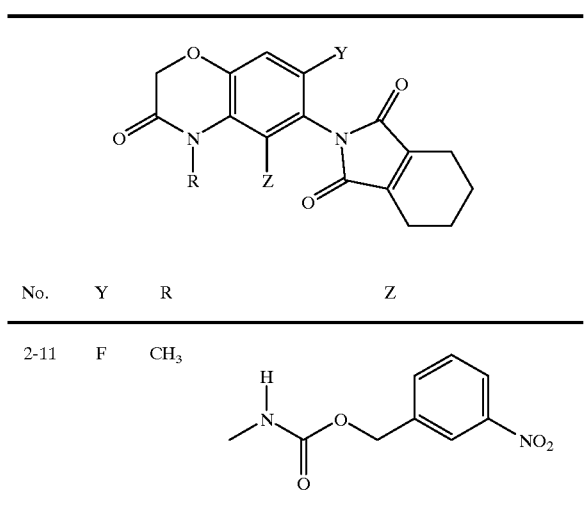

| No. | Y | R | Z |
|---|---|---|---|
| 2-11 | F | CH₃ | (N-methylcarbamate of 3-nitrobenzyl alcohol) |

TABLE 3

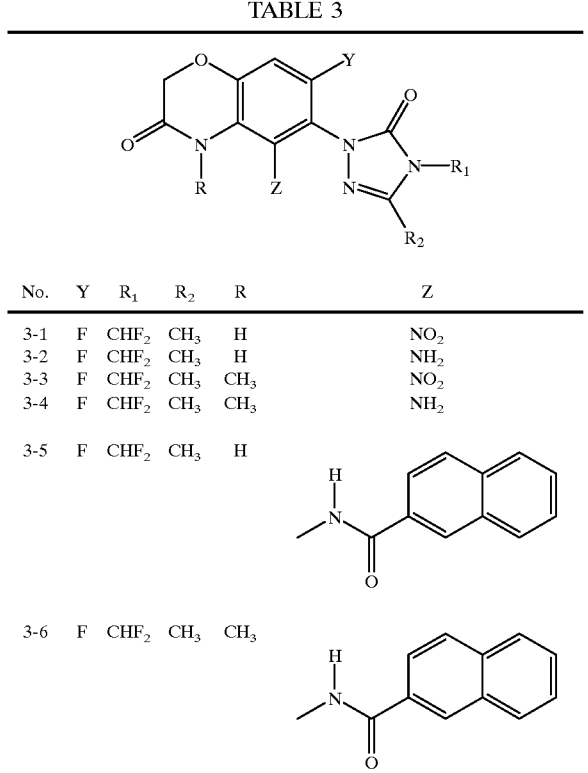

| No. | Y | R₁ | R₂ | R | Z |
|---|---|---|---|---|---|
| 3-1 | F | CHF₂ | CH₃ | H | NO₂ |
| 3-2 | F | CHF₂ | CH₃ | H | NH₂ |
| 3-3 | F | CHF₂ | CH₃ | CH₃ | NO₂ |
| 3-4 | F | CHF₂ | CH₃ | CH₃ | NH₂ |
| 3-5 | F | CHF₂ | CH₃ | H | (N-methyl-2-naphthamide) |
| 3-6 | F | CHF₂ | CH₃ | CH₃ | (N-methyl-2-naphthamide) |

TABLE 3-continued

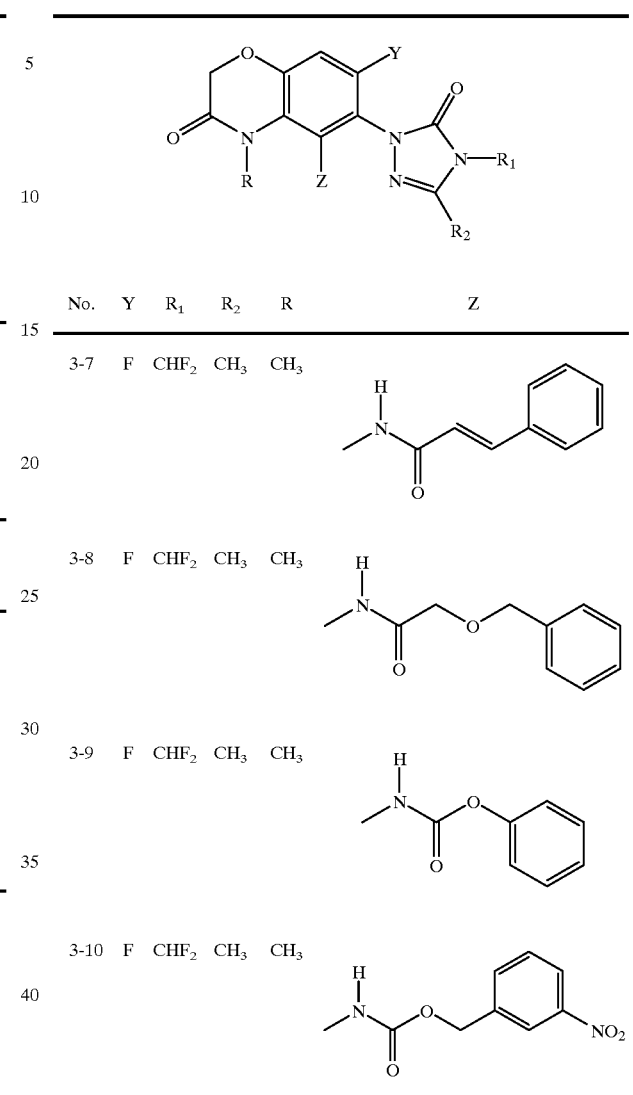

| No. | Y | R₁ | R₂ | R | Z |
|---|---|---|---|---|---|
| 3-7 | F | CHF₂ | CH₃ | CH₃ | (N-methyl cinnamamide) |
| 3-8 | F | CHF₂ | CH₃ | CH₃ | (N-methyl 2-benzyloxyacetamide) |
| 3-9 | F | CHF₂ | CH₃ | CH₃ | (N-methyl phenyl carbamate) |
| 3-10 | F | CHF₂ | CH₃ | CH₃ | (N-methyl 3-nitrobenzyl carbamate) |

TABLE 4
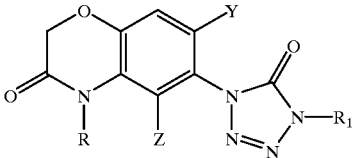
| No. | Y | R₁ | R | Z |
|---|---|---|---|---|
| 4-1 | F | 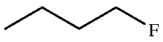 | H | $NO_2$ |
| 4-2 | F | 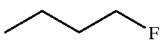 | H | $NH_2$ |
| 4-3 | F | 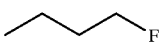 | $CH_3$ | $NO_2$ |
| 4-4 | F | 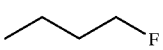 | $CH_3$ | $NH_2$ |
| 4-5 | F | 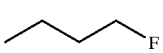 | H | 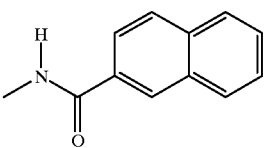 |
| 4-6 | F | 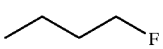 | $CH_3$ | 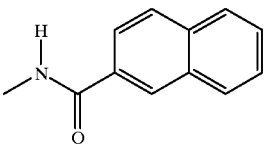 |
| 4-7 | F | 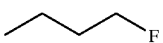 | $CH_3$ | 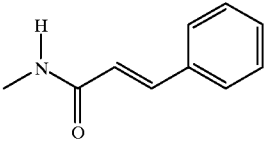 |
| 4-8 | F | 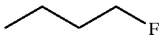 | $CH_3$ | 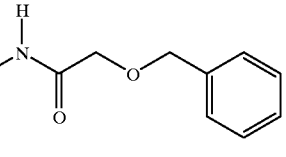 |
| 4-9 | F | 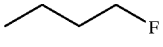 | $CH_3$ | 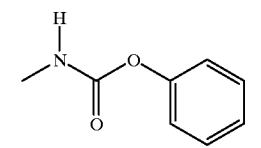 |
| 4-10 | F | 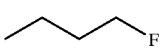 | $CH_3$ | 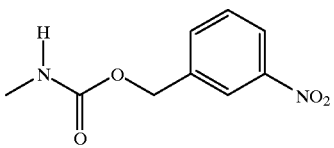 |

TABLE 5

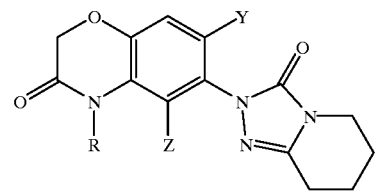

| No. | Y | R | Z |
|---|---|---|---|
| 5-1 | F | H | NO₂ |
| 5-2 | F | H | NH₂ |
| 5-3 | F | CH₃ | NO₂ |
| 5-4 | F | CH₃ | NH₂ |
| 5-5 | F | H | (N-methyl 2-naphthamide) |
| 5-6 | F | CH₃ | (N-methyl 2-naphthamide) |
| 5-7 | F | CH₃ | (N-methyl cinnamamide) |
| 5-8 | F | CH₃ | (N-methyl benzyloxyacetamide) |
| 5-9 | F | CH₃ | (N-methyl phenyl carbamate) |
| 5-10 | F | CH₃ | (N-methyl 3-nitrobenzyl carbamate) |

TABLE 6

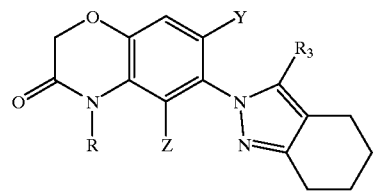

| No. | Y | R₃ | R | Z |
|---|---|---|---|---|
| 6-1 | F | Cl | H | NO₂ |
| 6-2 | F | Cl | H | NH₂ |
| 6-3 | F | Cl | CH₃ | NO₂ |
| 6-4 | F | Cl | CH₃ | NH₂ |
| 6-5 | F | Cl | H | (N-methyl 2-naphthamide) |
| 6-6 | F | Cl | CH₃ | (N-methyl 2-naphthamide) |
| 6-7 | F | Cl | CH₃ | (N-methyl cinnamamide) |
| 6-8 | F | Cl | CH₃ | (N-methyl benzyloxyacetamide) |
| 6-9 | F | Cl | CH₃ | (N-methyl phenyl carbamate) |
| 6-10 | F | Cl | CH₃ | (N-methyl 3-nitrobenzyl carbamate) |

TABLE 7
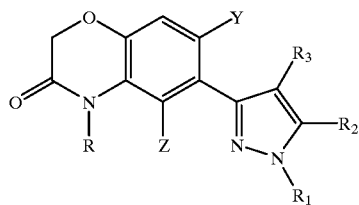
| No. | Y | R₁ | R₂ | R₃ | R | Z |
|---|---|---|---|---|---|---|
| 7-1 | F | CH₃ | CF₃ | Br | H | NO₂ |
| 7-2 | F | CH₃ | CF₃ | Br | H | NH₂ |
| 7-3 | F | CH₃ | CF₃ | Br | CH₃ | NO₂ |
| 7-4 | F | CH₃ | CF₃ | Br | CH₃ | NH₂ |
| 7-5 | F | CH₃ | OCHF₂ | Cl | H | NO₂ |
| 7-6 | F | CH₃ | OCHF₂ | Cl | H | NH₂ |
| 7-7 | F | CH₃ | OCHF₂ | Cl | CH₃ | NO₂ |
| 7-8 | F | CH₃ | OCHF₂ | Cl | CH₃ | NH₂ |
| 7-9 | F | CH₃ | CF₃ | Br | H | 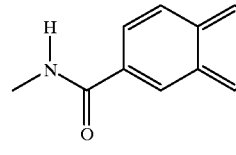 |
| 7-10 | F | CH₃ | CF₃ | Br | CH₃ | 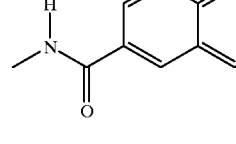 |
| 7-11 | F | CH₃ | OCHF₂ | Cl | H | 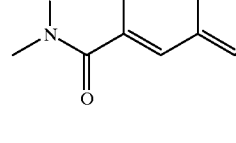 |
| 7-12 | F | CH₃ | OCHF₂ | Cl | CH₃ | 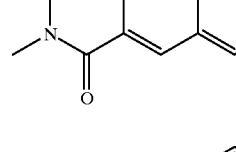 |
| 7-13 | F | CH₃ | CF₃ | Br | CH₃ | 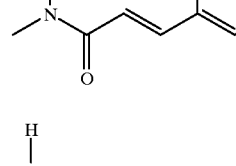 |
| 7-14 | F | CH₃ | CF₃ | Br | CH₃ | 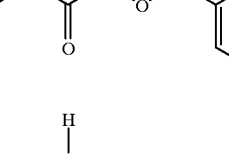 |
| 7-15 | F | CH₃ | CF₃ | Br | CH₃ | 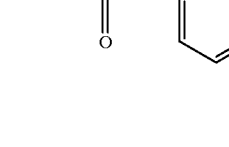 |

TABLE 7-continued

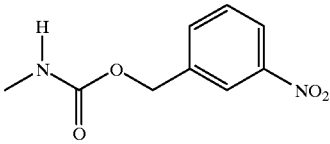

| No. | Y | $R_1$ | $R_2$ | $R_3$ | R | Z |
|---|---|---|---|---|---|---|
| 7-16 | F | $CH_3$ | $CF_3$ | Br | $CH_3$ | 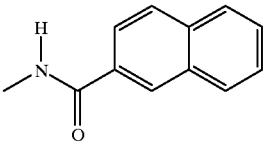 |
| 7-17 | F | $CH_3$ | $OCHF_2$ | Cl | $CH_3$ | 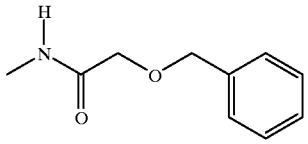 |
| 7-18 | F | $CH_3$ | $OCHF_2$ | Cl | $CH_3$ | 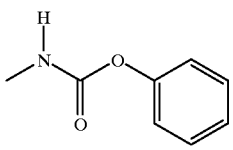 |
| 7-19 | F | $CH_3$ | $OCHF_2$ | Cl | $CH_3$ | 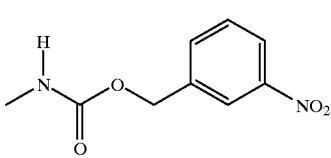 |
| 7-20 | F | $CH_3$ | $OCHF_2$ | Cl | $CH_3$ |  |

Table lists some of the characterization data for a few representative compounds of this invention.

TABLE

| No. | $^1$H NMR data<br>NMR (CDCl$_3$, 300 MHz) ppm |
|---|---|
| 1-1 | 4.73 (2H, s), 6.16 (1H, s), 7.19 (1H, d, J = 9.1 Hz) |
| 1-2 | 3.17 (3H, s), 3.56 (3H, s), 4.72 (2H, s), 6.35 (1H, s), 7.16 (1H, d, J = 9.0 Hz) |
| 1-3 | 4.51 (2H, s), 4.74 (2H, s), 6.15 (1H, s), 6.25 (1H, d, J = 9.9 Hz), 10.07 (1H, s) |
| 1-4 | 3.36 (3H, s), 3.56 (3H, s), 3.92 (2H, b), 4.48 (2H, s), 6.36 (1H, s), 6.42 (1H, d, J = 9.7 Hz) |
| 1-5 | 3.48 (3H, s), 3.56 (3H, s), 4.55 (2H, s), 6.04 (1H, s), 6.36 (1H, s), 6.49 (1H, s), 6.81 (1H, d, J = 9.5 Hz) |
| 1-6 | 3.51 (3H, s), 4.26 (2H, s), 4.43 (2H, s), 6.29 (1H, d, J = 9.9 Hz), 6.30 (1H, s), 10.18 (1H, s) |
| 1-7 | 2.48 (1H, t, J = 2.3 Hz), 3.56 (3H, s), 4.50 (2H, d, J = 2.3 Hz), 4.54 (2H, s), 4.67 (2H, s), 6.37 (1H, s), 6.38 (1H, d, J = 10.5 Hz) |
| 1-8 | 2.67 (3H, s), 3.39 (3H, s), 3.58 (3H, s), 4.53 (2H, s), 6.38 (1H, s), 6.56 (1H, d, J = 9.7 Hz) |
| 1-9 | 3.51 (3H, s), 3.58 (3H, s), 4.59 (2H, s), 6.36 (1H, s), 6.94 (1H, d, J = 9.1 Hz) |
| 1-10 | 1.18 (9H, s), 3.55 (3H, s), 4.58 (2H, s), 6.31 (1H, s), 6.84 (1H, d, J = 9.6 Hz), 8.28 (1H, s), 9.31 (1H, s) |
| 1-11 | 1.28 (3H, t, J = 7.2 Hz), 3.55 (3H, s), 4.17 (2H, s), 4.24 (2H, q, J = 7.1 Hz), 4.67 (2H, s), 4.82 (2H, s), 6.21 (1H, d, J = 10.5 Hz), 6.35 (1H, s) |
| 1-12 | 3.22 (3H, s), 3.48 (3H, s), 4.29 (2H, s), 6.22 (1H, s), 6.87 (1H, d, J = 9.5 Hz), 7.56 (2H, m), 7.80 (4H, m), 8.32 (2H, m) |
| 1-13 | 3.41 (3H, s), 4.16 (2H, m), 6.18 (1H, s), 6.62 (1H, b), 7.56 (2H, m), 7.85 (4H, m), 8.30 (2H, m), 9.12 (1H, b) |

TABLE-continued

¹H NMR data

| No. | NMR (CDCl₃, 300 MHz) ppm |
|---|---|
| 1-14 | 1.21 (3H, m), 3.30 (2H, m), 3.41 (3H, s), 3.58 (3H, s), 4.13 (2H, m), 4.29 (1H, m), 4.53 (2H, m), 6.38 (1H, s), 6.94 (1H, d, J = 9.2 Hz) |
| 1-15 | 1.22 (3H, t, J = 7.1 Hz), 3.57 (3H, s), 4.13 (2H, m), 4.53 (2H, s), 4.61 (2H, s), 4.71 (2H, s), 6.33 (1H, s), 6.69 (1H, d, J = 9.8 Hz) |
| 1-16 | 3.37 (3H, s), 4.07 (2H, s), 4.54 (2H, s), 4.58 (2H, s), 6.16 (2H, s), 6.84 (1H, d, J = 9.8 Hz), 7.29 (5H, m), 8.22 (1H, s), 8.85 (1H, s) |
| 1-17 | 3.47 (3H, s), 4.51 (2H, s), 4.63 (2H, m), 6.24 (1H, s), 6.78 (1H, d, J = 9.8 Hz), 7.21 (1H, m), 7.47 (1H, m), 7.70 (1H, m), 7.88 (1H, m), 8.31 (1H, s), 9.27 (1H, s) |
| 1-18 | 3.50 (3H, s), 4.51 (2H, m), 6.28 (1H, s), 6.79 (1H, m), 7.36 (6H, m), 7.61 (1H, d, J = 10.1 Hz), 7.89 (1H, s), 9.36 (1H, s) |
| 1-19 | 3.52 (3H, s), 4.60 (2H, s), 6.34 (1H, s), 6.82 (1H, m), 6.92 (1H, d, J = 9.8 Hz), 7.00 (1H, m), 8.01 (1H, m), 8.50 (1H, m), 8.93 (1H, m) |
| 1-20 | 3.51 (3H, s), 3.59 (3H, s), 4.58 (2H, s), 6.40 (1H, s), 6.85 (1H, d, J = 9.3 Hz) |
| 1-21 | 3.43 (3H, s), 3.50 (3H, s), 4.56 (2H, s), 6.37 (1H, s), 6.83 (1H, s), 6.95 (1H, d, J = 9.5 Hz), 7.01 (2H, m), 7.21 (1H, m), 7.34 (2H, m) |
| 1-22 | 3.21 (3H, s), 3.53 (3H, s), 4.51 (2H, m), 5.18 (2H, m), 6.32 (1H, s), 6.70 (1H, b), 6.92 (1H, d, J = 9.5 Hz), 7.57 (2H, m), 8.16 (2H, m) |
| 1-23 | 0.7–1.2 (8H, m), 1.96 (1H, m), 2.15 (1H, m), 3.18 (3H, s), 3.55 (3H, s), 4.54 (2H, m), 6.35 (1H, m), 7.03 (1H, d, J = 9.2 Hz) |
| 1-24 | 3.57 (3H, s), 4.76 (2H, s), 6.37 (1H, s), 7.21 (1H, d, J = 9.0 Hz), 9.30 (1H, s) |
| 1-25 | 3.51 (3H, s), 4.54 (2H, s), 6.36 (1H, s), 6.93 (1H, d, J = 9.7 Hz), 7.87–8.03 (3H, m), 8.24 (1H, m), 8.94 (1H, s), 9.59 (1H, s), 9.65 (1H, s) |
| 2-1 | 1.84 (4H, m), 2.44 (4H, m), 4.74 (2H, s), 7.17 (1H, d, J = 9.0 Hz), 9.10 (1H, s) |
| 2-2 | (DMSO-d6) 1.74 (4H, m), 2.31 (4H, m), 4.56 (2H, s), 5.69 (2H, s), 6.25 (1H, d, J = 10.2 Hz), 10.02 (1H, s) |
| 2-3 | 1.84 (4H, m), 2.44 (4H, m), 3.18 (3H, s), 4.70 (2H, s), 7.11 (1H, d, J = 8.9 Hz) |
| 2-4 | 1.84 (4H, m), 2.45 (4H, m), 3.40 (3H, s), 4.49 (2H, s), 6.39 (1H, d, J = 9.6 Hz) |
| 2-5 | 1.71 (4H, m), 2.38 (4H, m), 3.27 (3H, s), 4.56 (2H, s), 6.94 (1H, d, J = 9.6 Hz), 7.50–7.65 (2H, m), 7.70–7.95 (4H, m), 8.15 (1H, m), 8.32 (1H, m) |
| 2-6 | 1.82 (4H, m), 2.42 (4H, m), 3.19 (3H, s), 4.64 (2H, s), 6.80–7.10 (3H, m), 8.09 (1H, m), 8.21 (1H, m) |
| 3-1 | 2.49 (3H, s), 4.75 (2H, s), 7.04 (1H, t, J = 58.0 Hz), 7.17 (1H, d, J = 9.2 Hz), 9.2 (1H, br s) |
| 4-1 | 2.30 (2H, dt, J = 26.2, 5.7 Hz), 4.21 (2H, t, J = 5.8 Hz), 4.58 (2H, dt, J = 46.8, 5.6 Hz), 4.79 (2H, s), 7.25 (1H, d, J = 9.3 Hz), 9.21 (1H, s). |
| 4-2 | (DMSO-d₆) 2.20 (2H, ddd, J = 26.4, 6.1, 6.0 Hz), 4.06 (2H, t, J = 6.7 Hz), 4.59 (2H, dt, J = 47.1, 5.6 Hz), 4.59 (2H, s), 5.86 (2H, s), 6.31 (1H, d, J = 10.3 Hz), 10.13 (1H, s). |
| 4-3 | 2.29 (2H, dt, J = 26.5, 5.7 Hz), 3.18 (3H, s), 4.20 (2H, t, J = 6.8 Hz), 4.57 (2H, dt, J = 46.9, 5.5 Hz), 4.75 (2H, s), 7.21 (1H, d, J = 9.0 Hz), 9.21 (1H, s). |
| 4-4 | (Acetone-d₆) 2.28 (2H, ddd, J = 26.2, 6.4, 6.1 Hz), 3.36 (3H, s), 4.15 (2H, t, J = 6.9 Hz), 4.53 (2H, s), 4.62 (2H, dt, J = 47.3, 5.5 Hz), 5.27 (2H, br s), 6.39 (1H, d, J = 10.1 Hz). |

HERBICIDAL ACTIVITY

The compounds of the present invention exhibit excellent herbicidal effects when used as an active ingredient of a herbicide. The herbicide can be used for a wide range of applications, for example on crop lands such as paddy fields, upland farms, orchards and mulberry fields, and non-crop lands such as forests, farm roads, playgrounds, and factory sites. The application method may be suitably selected for soil treatment application and foliar application.

The compounds of the present invention are capable of controlling noxious weeds including grass (gramineae) such as barnyardgrass (*Echinochloa crus-galli*), large crabgrass (*Digitaria sanguinalis*), green foxtail (*Setaria viridis*), goosegrass (*Eleusine indica* L.), wild oat (*Avena fatua* L.), Johnsongrass (*Sorghum halepense*), quackgrass, (*Agropyron repens*), alexandergrass (*Brachiaria plantaginea*), paragrass (*Panicum purpurascen*), sprangletop (*Leptochloa chinensis*) and red sprangletop (*Leptochloa panicea*); sedges (or Cyperaceae) such as rice flatsedge (*Cyperus iria* L.), purple nutsedge (*Cyperus rotundus* L.), Japanese bulrush (*Scirpus Juncoides*), flatsedge, (*Cyperus serotinus*), small-flower umbrellaplant (*Cyperus difformis*), slender spikerush (*Eleocharis acicularis*), and water chestnut (*Eleochars kuroguwai*); alismataceae such as Japanese ribbon wapato (*Sagittaria pygmaea*), arrow-head (*Sagittaria trifolia*) and narrowleaf waterplantain (*Alisma canaliculatum*); pontederiaceae such as monochoria (*Monochoria vaginalis*) and monochoria species (*Monochoria korsakowii*); scrophulariaceae such as false pimpernel (*Lindernia pyxidaria*) and abunome (*Dopatrium Junceum*); lythraceae such as toothcup (*Rotala indica*) and red stem, (*Ammannia multiflora*); and broadleaves such as redroot pigweed (*Amaranthus retroflexus*), velvetleaf (*Abutilon theophrasti*), morningglory (*Ipomoea hederacea*), lambsquarters (*Chenopodium album*), prickly sida (*Sida spinosa* L.), common purslane (*Portulaca oleracea* L.), slender amaranth (*Amaranthus viridis* L.), sicklepod (*Cassia obtusifolia*), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis*L.). Accordingly, it is useful for controlling noxious weeds non-selectively or selectively in the cultivation of a crop plant such as corn (*Zea mays* L.), soybean (*Glycine max* Merr.), cotton (Gossypium spp.), wheat (Triticum spp.), rice (*Oryza sativa* L.), barley (*Hordezum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), Japanese lawngrass (*Zoysia Japonica stend*), peanut (*Arachis hypogaea* L.) or flax (*Linum usitatissimum* L.).

For use as herbicides, the active ingredients of this invention are formulated into herbicidal compositions by mixing herbicidally active amounts with inert ingredients known to the art to facilitate either the suspension, dissolution or emulsification of the active ingredient for the desired use. The type of formulation prepared recognizes the facts that formulation, crop and use pattern all can influence the activity and utility of the active ingredient in a particular use. Thus for agricultural use the present herbicidal compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These herbicidal formulations may be applied to the target area (where suppression of unwanted vegetation is the objective) as dusts, granules or water or solvent diluted sprays. These formulation may contain as little as 0.1% to as much as 97% active ingredient by weight.

Dusts are admixtures of the active ingredient with finely ground materials such as clays (some examples include kaolin and montmorillonite clays), talc, granite dust or other organic or inorganic solids which act as dispersants and carriers for the active ingredient; these finely ground materials have an average particle size of less than 50 microns. A typical dust formulation will contain 1% active ingredient and 99% carrier.

Wettable powders are composed of finely ground particles which disperse rapidly in water or other spray carriers.

Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredient with the granules with or without a sticking agent to facilitate adhesion of the active ingredient to the granule surface, or by dissolving the active ingredient in a solvent, spraying the dissolved active ingredient and solvent onto the granule then drying to remove the solvent. Granular formulations are useful where in-furrow or banded application is desired.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredient (5 to 50% by weight), carrier, wetting agent, dispersing agent, anti-freeze, viscosity modifiers and pH modifiers. For application, suspension concentrates are typically diluted with water and sprayed on the target area.

Solution concentrates are solutions of the active ingredient (1 to 70%) in solvents which have sufficient solvency to dissolve the desired amount of active ingredient. Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient is made as a suspension concentrate (1–50% active ingredient) and the second active is made as a emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The herbicidal compounds of this invention may be formulated or applied with insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UV protectants may be added in amounts of 0.01% to 5% to enhance the biological activity, stability, wetting, spreading on foliage or uptake of the active ingredients on the target area or to improve the suspensibility, dispersion, redispersion, emulsifiability, UV stability or other physical or physicochemical property of the active ingredient in the spray tank, spray system or target area.

The compositions of the present invention may be used in admixture with or in combination with other agricultural chemicals, fertilizers, adjuvants, surfactants, emulsifiers, oils, polymers or phytotoxicity-reducing agents such as herbicide safeners. In such a case, they may exhibit even better effects or activities. As other agricultural chemicals, herbicides, fungicides, antibiotics, plant hormones, plant growth regulators, insecticides, or acaricides may, for example, be mentioned. Especially with herbicidal compositions having the compounds of the present invention used in admixture with or in combination with one or more active ingredients of other herbicides, it is possible to improve the herbicidal activities, the range of application time(s) and the range of applicable weed types. Further, the compounds of the present invention and an active ingredient of another herbicide may be separately formulated so they may be mixed for use at the time of application, or both may be formulated together. The present; invention covers such herbicidal compositions.

The blend ratio of the compounds of the present invention with the active ingredient of other herbicides can not generally be defined, since it varies depending on the time and method of application, weather conditions, soil type and type of formulation. However one active ingredient of other herbicide may be incorporated usually in an amount of 0.01 to 100 parts by weight, per one part by weight of the compounds of the present invention. Further, the total dose of all of the active ingredients is usually from 1 to 10000 g/ha, preferably from 5 to 500 g/ha. The present invention covers such herbicidal compositions.

As the active ingredients of other herbicides, the following (common name) may be mentioned. Herbicidal compositions having the compounds of the present invention used in combination with other herbicides, may occasionally exhibit a synergistic effect.

Those that are believed to exhibit herbicidal effects by disturbing auxin activities of plants, including a phenoxy acetic acid type such as 2,4-D, 2,4-DB, 2,4-DP, MCPA, MCPP, MCPB or naproanilide (including the free acids, esters or salts thereof), an aromatic carboxylic type such as 2,3,6 TBA, dicamba, dichlobenil, a pyridine type such as picloram (including free acids and salts thereof), triclopyr or clopyralid and others such as naptalam, benazolin, quinclorac, quinmerac or diflufenzopyr (BAS 654H).

Those that are believed to exhibit herbicidal effects by inhibiting photosynthesis of plants including a urea type such as diuron, linuron, isoproturon, chlorotoluron, metobenzuron, tebuthiuron or fluometuron, a triazine type such as simazine, atrazine, cyanazine, terbuthylazine, atraton, hexazinone, metribuzin, simetryn, ametryn, prometryn, dimethametryn or triaziflam, a uracil type such as bromacil, terbacil or lenacil, an anilide type such as propanil or cypromid, a carbamate type such as desmedipham or phenmedipham, a hydroxybenzonitrile type such as bromoxynil or ioxynil, and others such as pyridate, bentazon and methazole.

A quaternary ammonium salt type such as paraquat, diquat or difenzoquat, which is believed to be converted to free radicals by itself to form active oxygen in the plant and thus to exhibit quick herbicidal effects.

Those which are believed to exhibit herbicidal effects by inhibiting chlorophyll biosynthesis in plants and abnormally accumulating a photsensitizing substance in the plant body, including a diphenyl ether type such as nitrofen, lactofen, acifluorfen-sodium, oxyfluorfen, fomesafen, bifenox, or chlomethoxyfen, a cyclic imide type such as chlorphthalim, flumioxazin, cinidon-ethyl, or flumiclorac-pentyl, and others such as oxadiazon, sulfentrazone, thidiazimin, azafenidin, carfentrazone, isopropazole, fluthiacet-methyl, pentoxazone, pyraflufen-ethyl and oxadiargyl.

Those which are believed to exhibit herbicidal effects characterized by whitening activities by inhibiting chromogenesis of plants such as carotenoids including a pyridazinone type such as norflurazon, chloridazon or metflurazon, a pyrazol type such as pyrazolate, pyrazoxyfen or benzofenap, and others such as fluridone, fluramone, difiufencam, methoxyphenone, clomazone, amitrole, sulcotrione, mesotrione, isoxaflutole and isoxachlortole.

Those which exhibit herbicidal effects specifically to gramineous plants including an aryloxyphenoxypropionic acid type (either as a mixture of isomers or as a resolved isomer) such as diclofop-methyl, pyrofenop-sodium, fluazifop butyl or fluazifop-p-butyl, haloxyfop-methyl, quizalofop p-ethyl, quizalafop p-tefuryl, fenoxaprop ethyl or fenoxaprop-p-ethyl, flamprop-M-methyl or flamprop-m-isopropyl or cyhalofop-butyl and a cyclohexanedione type such as alloxydim-sodium, sethoxydim, clethodim, tepraloxydim or tralkoxydim.

Those which are believed to exhibit herbicidal effects by inhibiting amino acid biosynthesis of plants, including a sulfonylurea type such as chlorimuron-ethyl, nicosulfuron, metsulfuron-methyl, triasulfuron, primisulfuron, tribenuron-methyl, chlorosulfuron, bensulfuron-methyl, sulfometuron-methyl, prosulfuron, halosulfuron or halosulfuron-methyl, thifensulfuron-methyl, rimsulfuron, azimsulfuron, flazasulfuron, imazosulfuron, cyclosulfamuron, flupyrsulfuron, iodosulfuron, ethoxysulfuron, flucarbazone, sulfosulfuron, oxasulfuron a triazolopyrimidinesulfonamide type such as flumetsulam, metosulam, chloransulam or chloransulam-methyl, an imidazolinone type such as imazapyr, imazethapyr, imazaquin, imazamox, imazameth, imazamethabenz methyl, a pyrimidinesalicylic acid type such as pyrthiobac-sodium, bispyribac-sodium, pyriminobac-methyl or pyribenzoxim (LGC-40863), and others such as glyphosate, glyphosate-ammonium, glyphosate-isopropylamine or sulfosate.

Those which are believed to exhibit herbicidal effects by interfering with the normal metabolism of inorganic nitrogen assimilation such as glufosinate, glufosinate-ammonium, phosphinothricin or bialophos.

Those which are believed to exhibit herbicidal effects by inhibiting cell division of plant cells, including a dinitroaniline type such as trifluralin, oryzalin, nitralin, pendamethalin, ethafluralin, benefin and prodiamine, an amide type such as bensulide, napronamide, and pronamide, a carbamate type such as propham, chlorpropham, barban, and asulam, an organophosphorous type such as amiprofos-methyl or butamifos and others such as DCPA and dithiopyr.

Those which are believed to exhibit herbicidal effects by inhibiting protein synthesis of plant cells, including a chloroacetanilide type such as alachlor, metolachor (including combinations with safeners such as benoxacor, or resolved isomeric mixtures of metolachlor including safeners such as benoxacor) propachlor, acetochlor (including combinations with herbicide safeners such as dichlormid or MON 4660 or resolved isomeric mixtures of acetochlor containing safeners such as dichlormid or MON 4660), propisochlor or dimethenamid or an oxyacetamide type such as flufenacet.

Those in which the mode of action causing the herbicidal effects are not well understood including the dithiocarbamates such as thiobencarb, EPTC, diallate, triallate, molinate, pebulate, cycloate, butylate, vernolate or prosulfocarb and miscellaneous herbicides such as MSMA, DSMA, endothall, ethofumesate, sodium chlorate, pelargonic acid and fosamine.

A few formulation examples of the present invention are given as follows:

FORMULATION EXAMPLE 1

Emulsifiable Concentrate

| Ingredient Trade Name | Chemical Name | Supplier | Function | % wt./wt. |
|---|---|---|---|---|
| | | | Active Ingredient | 5.0 |
| Toximul H-A | Calcium sulfonate and nonionic surfactant blend | Stepan Co. | Emulsifier | 2.5 |
| Toximul D-A | Calcium sulfonate and nonionic surfactant blend | Stepan Co. | Emulsifier | 7.5 |
| Aromatic 200 | Aromatic hydrocarbon | Exxon Chemical Co. | Solvent | QS to 100% |

FORMULATION EXAMPLE 2
Suspension Concentrate

| Ingredient Trade Name | Chemical Name | Supplier | Function | % wt./wt. |
|---|---|---|---|---|
| | | | Active Ingredient | 10.00 |
| Proylene gylcol | | | Anti-freeze | 5.00 |
| Antifoam 1530 | Silicone defoamer | Dow Corning | Anti-foam | 0.50 |
| Rhodopol 23 | Xanthan gum | Rhone-Poulenc | Suspending Aid | 0.25 |
| Morwet D-425 | Napthalene formaldehyde condensate | Witco Corp. | Dispersant | 3.00 |
| Igepal CA-720 | Octylphenol ethoxylate | Rhone-Poulenc | Wetting agent | 3.00 |
| Proxel GXL | 1,2 benziso-thiazolin-3-one | ICI Americas | Preservative | 0.25 |
| Water | | | Diluent | 68.00 |

FORMULATION EXAMPLE 3
Wettable Powder

| Ingredient Trade Name | Chemical Name | Supplier | Function | % wt./wt. |
|---|---|---|---|---|
| | | | Active Ingredient | 50.00 |
| Geropon T-77 | Sodium N-methyl-N-oleoyltaurate | Rhone-Poulenc | Wetting agent | 3.00 |
| Lomar PW | Napthalene Sulfonate | Henkel Corp. | Dispersant | 5.00 |
| Kaolin clay | Kaolin clay | J. M. Huber | Filler | 42.00 |

FORMULATION EXAMPLE 4
Water Dispersible Granule

| Ingredient Trade Name | Chemical Name | Supplier | Function | % wt./wt. |
|---|---|---|---|---|
| | | | Active Ingredient | 50.00 |
| Morwet EFW | | Witco Corp. | Wetting agent | 2.00 |
| Morwet D-425 | Napthalene formaldehyde condensate | Witco Corp. | Dispersant | 10.00 |
| ASP 400 | Kaolin Clay | Engelhard Corp. | Filler | 38.00 |

TEST EXAMPLE

A standard greenhouse herbicide activity screening system was used to evaluate the herbicidal efficacy and crop safety of these test compounds. Seven broadleaf weed species including redroot pigweed (*Amaranthus retroflexus*, AMR), velvetleaf (*Abutilon theophrasti*, ABT), sicklepod (*Cassia obtusifolia*, CAO), ivyleaf morningglory (*Ipomoea hederacea*, IPH), lambsquarters (*Chenopodium album*, CHA), common ragweed (*Ambrosia artemisijfolia* L., AML), and cocklebur (*Xanthium strumarium*, XAS) were used as test species. Four grass weed species including green foxtail (*Setaia viridis*, SEV), barnyardgrass (*Echinochloa crus-galli*, ECC), johnsongrass (*Sorghum halepense*, SOH), and large crabgrass (*Digitania sanguinalis*, DIS) were also used. In addition, four crop species, field corn (*Zea mays* L., var. Dekalb 535, CORN), soybean (*Glycine max* L., var. Pella 86, SOY), upland rice (*Oryza* sp., var.Tebonnet, RICE), and wheat (*Triticum aestivum*) were included. All plants were grown in 10 cm square plastic pots which were filled with a sandy loam soil mix.

Pre-emerge Test

For pre-emerge tests, seeds were planted one day prior to application of the test compounds. All test compounds were dissolved in acetone and applied to the test pots in a volume of 187 l/ha. Test materials were applied at rates ranging from 8 g ai/ha to 1000 g ai/ha using a track sprayer equipped with a TJ8001E even flow flat fan spray nozzle. This application simulates a typical commercial field herbicide application.

Post-emerge Test

For post-emerge tests, seeds were planted 8–21 days prior to the test to allow emergence and good foliage development prior to application of the test substances. At the time of the post-emerge application, plants of all species were usually at the 2–3 leaf stage of development. In the post-emerge test, a commercial non-ionic surfactant was also included (0.25% v/v) to enhance wetting of the leaf surfaces of target plants.

At 14 days after application of the test materials, phytotoxicity ratings were recorded. A rating scale of 0–100 was used for both pre and post emerge tests as previously described in *Research Methods in Weed Science,* 2nd edition, B. Truelove, Ed., Southern Weed Science Society, Auburn University, Auburn, Ala., 1977. Briefly, "0" corresponds to no damage and "100" corresponds to complete death of all plants in the test unit. This scale was used both to determine efficacy against weed species and damage to crop species. Herbicide activity data for various compounds of this invention, which are shown by compound No. in Tables 1–7, are shown in Tables. The data demonstrate significant differences between compounds for both efficacy against weeds and selectivity for crop species. For selected compounds, excellent activity against a majority of the weed species was observed with minimal damage to at least one of the crop species.

TABLE

Pre-emerge Herbicidal Activity

| Compd. No. | Rate g ai/ha | AMR | ABT | CAO | IPH | CHA | AML | XAS | SEV | ECC | SOH | DIS | CORN | SOY | RICE |
|---|---|---|---|---|---|---|---|---|---|---|---|---|---|---|---|
| 1-4 | 250 | 100 | 100 | 100 | 100 | 100 | 99 | 100 | 98 | 95 | 99 | 95 | 100 | 100 | 98 |
| 1-5 | 250 | 100 | 100 | 99 | 100 | 100 | 99 | 99 | 99 | 98 | 95 | 95 | 100 | 90 | 95 |
| 1-6 | 250 | 99 | 90 | 90 | 100 | 75 | 0 | 40 | 0 | 0 | 0 | 0 | 15 | 100 | 25 |
| 1-7 | 250 | 100 | 100 | 100 | 100 | 100 | 100 | 100 | 99 | 99 | 98 | 98 | 99 | 99 | 98 |
| 1-8 | 250 | 100 | 100 | 90 | 99 | 100 | 98 | 98 | 85 | 70 | 85 | 80 | 100 | 100 | 95 |

TABLE-continued

Pre-emerge Herbicidal Activity

| Compd. No. | Rate g ai/ha | AMR | ABT | CAO | IPH | CHA | AML | XAS | SEV | ECC | SOH | DIS | CORN | SOY | RICE |
|---|---|---|---|---|---|---|---|---|---|---|---|---|---|---|---|
| 1-10 | 250 | 0 | 55 | 10 | 50 | 0 | 35 | 40 | 0 | 0 | 0 | 0 | 15 | 35 | 25 |
| 1-11 | 250 | 80 | 60 | 70 | 75 | 90 | 55 | 65 | 0 | 0 | 0 | 0 | 0 | 0 | 0 |
| 1-12 | 250 | 100 | 100 | 98 | 100 | 100 | 99 | 55 | 100 | 100 | 100 | 100 | 100 | 55 | 99 |
| 1-13 | 250 | 100 | 100 | 98 | 100 | 100 | 100 | 55 | 99 | 98 | 60 | 100 | 10 | 15 | 80 |
| 1-15 | 250 | 0 | 80 | 30 | 60 | 80 | 0 | 30 | 0 | 15 | 5 | 0 | 95 | 10 | 30 |
| 1-16 | 250 | 100 | 100 | 100 | 100 | 100 | 100 | 100 | 100 | 99 | 99 | 100 | 100 | 100 | 99 |
| 1-17 | 250 | 100 | 100 | 85 | 100 | 100 | 100 | 100 | 100 | 99 | 98 | 100 | 60 | 35 | 90 |
| 2-1 | 250 | 100 | 100 | 60 | 75 | 98 | 75 | 30 | 80 | 75 | 80 | 75 | 10 | 0 | 20 |
| 2-4 | 250 | 100 | 100 | 50 | 99 | 100 | 35 | 50 | 55 | 65 | 75 | 50 | 35 | 0 | 55 |
| 2-5 | 250 | 100 | 100 | 50 | 75 | 100 | 98 | 30 | 80 | 80 | 35 | 99 | 0 | 35 | 60 |
| 2-6 | 250 | 99 | 100 | 60 | 60 | 100 | 70 | 75 | 40 | 25 | 55 | 60 | 100 | 35 | 85 |

TABLE

Post-emerge Herbicidal Activity

| Compd. No. | Rate g ai/ha | AMR | ABT | CAO | IPH | CHA | AML | XAS | SEV | ECC | SOH | DIS | CORN | SOY | RICE |
|---|---|---|---|---|---|---|---|---|---|---|---|---|---|---|---|
| 1-4 | 250 | 100 | 100 | 100 | 100 | 100 | 90 | 99 | 60 | 75 | 30 | 35 | 20 | 100 | 80 |
| 1-5 | 250 | 100 | 100 | 100 | 99 | 100 | 90 | 100 | 35 | 55 | 20 | 45 | 5 | 100 | 30 |
| 1-6 | 250 | 100 | 100 | 100 | 100 | 100 | 98 | 100 | 50 | 50 | 25 | 0 | 20 | 100 | 65 |
| 1-7 | 250 | 100 | 100 | 100 | 100 | 100 | 100 | 100 | 90 | 80 | 25 | 80 | 10 | 100 | 55 |
| 1-8 | 250 | 100 | 100 | 98 | 100 | 100 | 85 | 95 | 70 | 80 | 60 | 70 | 30 | 100 | 80 |
| 1-10 | 250 | 65 | 50 | 0 | 15 | 50 | 5 | 0 | 0 | 0 | 0 | 0 | 2 | 0 | 70 |
| 1-11 | 250 | 100 | 95 | 85 | 98 | 100 | 90 | 95 | 90 | 95 | 60 | 45 | 100 | 55 | 80 |
| 1-12 | 250 | 99 | 100 | 100 | 100 | 99 | 80 | 100 | 40 | 50 | 15 | 50 | 10 | 80 | 70 |
| 1-13 | 250 | 100 | 100 | 100 | 100 | 100 | 99 | 100 | 40 | 20 | 0 | 0 | 15 | 100 | 50 |
| 1-15 | 250 | 90 | 100 | 90 | 100 | 95 | 50 | 80 | 45 | 50 | 35 | 30 | 10 | 85 | 90 |
| 1-16 | 250 | 100 | 100 | 100 | 100 | 98 | 100 | 100 | 25 | 45 | 0 | 0 | 10 | 100 | 70 |
| 1-17 | 250 | 100 | 100 | 0 | 100 | 100 | 100 | 100 | 45 | 75 | 20 | 60 | 8 | 100 | 60 |
| 2-1 | 250 | 100 | 100 | 90 | 98 | 100 | 98 | 100 | 80 | 75 | 30 | 50 | 10 | 50 | 40 |
| 2-4 | 250 | 100 | 100 | 99 | 99 | 100 | 99 | 100 | 75 | 70 | 60 | 90 | 5 | 100 | 90 |
| 2-5 | 250 | 100 | 100 | 45 | 60 | 100 | 95 | 95 | 60 | 50 | 30 | 35 | 5 | 80 | 65 |
| 2-6 | 250 | 100 | 100 | 50 | 90 | 99 | 90 | 95 | 60 | 99 | 20 | 60 | 15 | 100 | 70 |

What is claimed is:

1. A compound represented by the formula (I) or its salt:

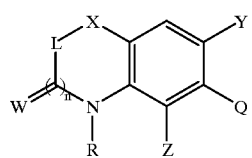

I wherein Q is a heterocycle selected from the group consisting of Q1 to Q24:

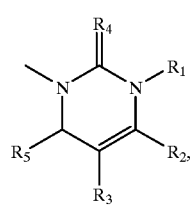

Q1

-continued

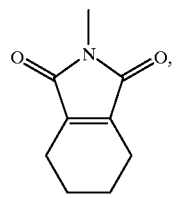

Q2

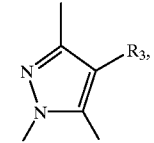

Q3

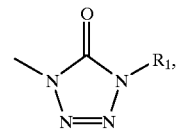

Q4

-continued
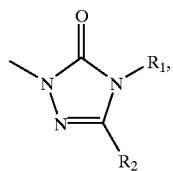
Q5
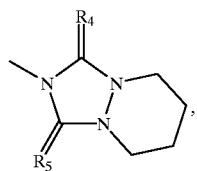
Q6
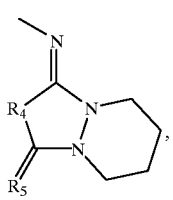
Q7
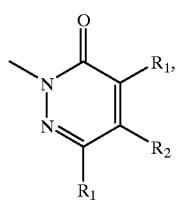
Q8
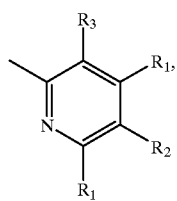
Q9
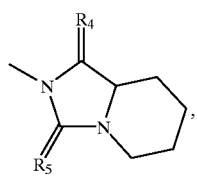
Q10
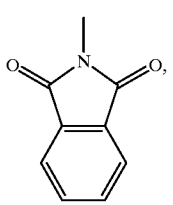
Q11
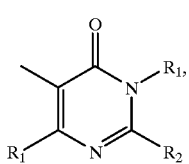
Q12
-continued
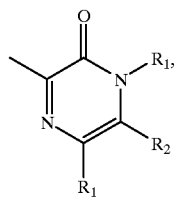
Q13
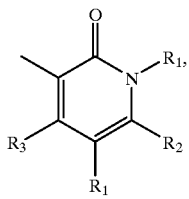
Q14
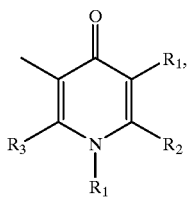
Q15
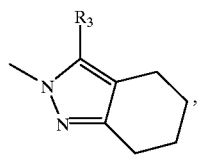
Q16
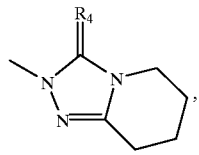
Q17
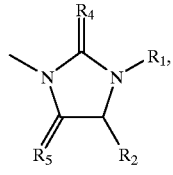
Q18
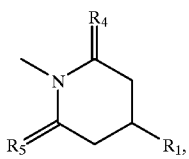
Q19
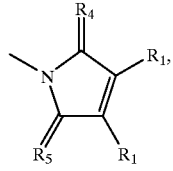
Q20

-continued

Q21
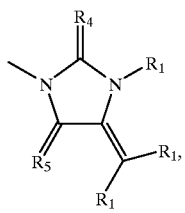

Q22
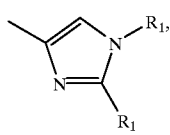

Q23
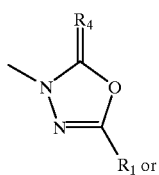

Q24
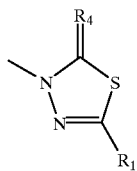

wherein $R_1$ is hydrogen, alkyl, haloalkyl, alkenyl, alkynyl, amino, alkoxyalkyl, acetyl, alkoxycarbonylamino, alkylcarbonylamino or alkoxycarbonyl;

$R_2$ is alkyl, haloalkyl, alkoxy, haloalkoxy or unsubstituted or substituted phenyl;

$R_3$ is hydrogen, halogen, nitro, amino, alkylamino, haloalkylamino, cyano or amide;

$R_4$ and $R_5$ are independently oxygen, sulfur or imino; Q6, Q7, Q10, Q16 or Q17 may be unsaturated containing one or two double bonds in the 6-membered ring;

R is hydrogen, alkyl, alkenyl, alkynyl, cycloalkyl, cycloalkylalkyl, alkoxyalkyl, alkoxyalkoxyalkyl, alkylcarbonyl, arylcarbonyl, alkoxycarbonyl, aryloxycarbonyl, alkoxycarbonylalkyl, alkoxyalkoxycarbonylalkyl, cycloalkoxycarbonylalkyl, aralkyl, heteroaralkyl, aryloxyalkyl or heteroaryloxyalkyl where any of these groups may be substituted with at least one substituent selected from the group consisting of halogen, cyano, nitro, amino, carboxyl, alkylthioalkyl, hydroxyalkyl, $CON(R_6)R_7$ and $COON(R_6)R_7$ $R_6$ and $R_7$ are independently hydrogen, halogen, alkyl, alkenyl, alkynyl, cycloalkyl, alkoxyalkyl, alkylthioalkyl, alkoxycarbonylalkyl, cycloalkoxycarbonylalkyl, alkylcarbonyloxyalkyl, alkylcarbonylaminoalkyl, alkoxyalkylcarbonylalkyl, phenyl or benzyl where any of these groups may be substituted with at least one substituent selected from the group consisting of halogen, cyano, carboxyl, hydroxy, nitro and amino;

W is O, S or imino;

n is an integer of 1;

—L—X— is —$CR_8R_9$—O—, or —$CR_8R_9$—S—;

$R_8$ and $R_9$ are independently hydrogen, halogen, alkyl, alkenyl, alkynyl, cycloalkyl, alkoxyalkyl, alkylthioalkyl, alkoxycarbonylalkyl, cycloalkoxycarbonylalkyl, alkylcarbonyloxyalkyl, alkylcarbonylaminoalkyl, alkoxyalkylcarbonylalkyl, phenyl or benzyl where any of these groups may be substituted with at least one substituent selected from the group consisting of halogen, cyano, carboxyl, hydroxy, nitro and amino;

Y is hydrogen or halogen;

Z is nitro, isocyanate, amino, hydroxyl, thiol, formyl, carboxyl, cyano, halogen, unsubstituted or substituted alkyl, alkenyl, alkylcarbonyl, arylcarbonyl, azido or one of the following:

wherein $R_{10}$ is alkyl, alkenyl, alkynyl, amino, cycloalkyl, heterocycloalkyl, alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heteroarylcarbonyl, alkoxycarbonyl, alkyithiocarbonyl, cycloalkyloxycarbonyl, aryloxycarbonyl, arylthio-carbonyl, arylthiocarbonyl, heteroaryloxycarbonyl, aminocarbonyl, alkylaminocarbonyl, arylaminocarbonyl, heteroarylaminocarbonyl, alkoxycarbonylcarbonyl or arylcarbonylcarbonyl where any of these groups may be substituted with at least one substituent selected from the group consisting of alogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkylthiocarbonyl, alkoxythiocarbonyl alkylaminocarbonyl, arylaminocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl and methylenedioxy, wherein the alkyl moiety or aryl moiety may be substituted with at least one substituent selected from the group consisting of halogen, cyano, nitro, alkyl, alkoxy, haloalkyl, haloalkoxy, alkoxycarbonyl, cycloalkyl, aryl and heterocycloalkyl;

$R_{11}$ is hydrogen or any one of the groups represented by $R_{10}$;

$R_{10}$ and $R_{11}$ may combine to form a 4–8 membered heterocyclic ring;

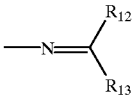

wherein $R_{12}$ is alkyl, haloalkyl, dialkylamino, unsubstituted or substituted aryl or heteroaryl;

$R_{13}$ is hydrogen, halogen or any of the groups represented by $R_{12}$

—$OR_{10}$, —$SR_{10}$, —$CH_2R_{14}$, —$CH(R_{14})_2$, —$C(R_{14})_3$ or —CH=$CHR_{14}$ wherein $R_{14}$ is carboxyl, alkyl, alkenyl, alkynyl, amino, cycloalkyl, heterocycloalkyl, alkylsulfonyl, arylsulfonyl, benzyl, aryl, heteroaryl, alkylcarbonyl, alkenylcarbonyl, alkynylcarbonyl, cycloalkylcarbonyl, arylcarbonyl, heterocrylcarbonyl, alkoxycarbonyl, alkyithiocarbonyl, cycloalkyloxycarbonyl, aryloxycarbonyl, arylthio-carbonyl, aryl-thiocarbonyl, heteroaryloxycarbonyl, aminocarbonyl, alkylaminocarbonyl, arylaminocarbonyl, heteroarylaminocarbonyl, alkoxycarbonylcarbonyl, or arylcarbonylcarbonyl where any of these groups may be substituted with at least one substituent selected from the group consisting of halogen, cyano, nitro, amino, dialkylamino, hydroxyl, carboxyl, alkyl, alkenyl, alkynyl, cycloalkyl, alkylcarbonyl, alkylcarbonyloxy, alkoxy, alkoxycarbonyl, alkylthio, alkythiocarbonyl, alkoxythiocarbonyl, alkylaminocarbonyl, aryla minocarbonyl, alkylsulfonyl, alkenyloxycarbonyl, alkynyloxycarbonyl, aryl, arylcarbonyl, aryloxy, aryloxycarbonyl, arylthio, heteroaryl, heteroaryloxycarbonyl and methylenedioxy, wherein the alkyl moiety or aryl moiety may be substituted with at least one substituent selected from the group consisting of halogen, cyano, nitro, alkyl, alkoxy, haloalkyl, haloalkoxy, alkoxycarbonyl, cycloalkyl, aryl and heterocycloalkyl.

2. The compound according to claim 1, wherein the formula (I) is:

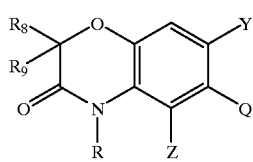

I-1 wherein Q, R, $R_8$, $R_9$ and Y are the same as defined in claim 1.

3. The compound according to claim 1, wherein Q is Q1–5, Q16 or Q17.

4. The compound according to claim 1, wherein Y is fluorine.

5. The compound according to claim 1, wherein the formula (I) is (I-1)

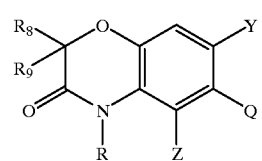

I-1

Wherein Q is Q1; Y is fluorine; and R, $R_8$, $R_9$ and Z are the same as defined in claim 1.

6. The compound of claim 5, wherein the compound is 3-[5-amino-7-fluoro-2H-1,4-benzoxazine-3(4H)-on-6-yl]-1-methyl-6-trifluoromethyl-2,4-(1H, 3H)-pyrimidinedione, 3-[5-(2-naphthoyl)amino-7-fluoro-2H-1,4-benzoxazine-3(4H)-on-6-yl]-1-methyl-6-trifluoromethyl-2,4-(1H,3H)-pyrimidinedione or 3-[5-cinnamoylamino-7-fluoro-2H-1,4-benzoxazine-3(4H)-on-6-yl]-1-methyl-6-trifluoromethyl-2, 4-(1H,3H)-pyrimidinedione.

7. The compound according to claim 1 that provided that
(1) Z is not nitro or amino, when Q is Q3 and $R_2$ is haloalkyl; and
(2) Z is not amino or

herein $R_{10}$ is alkyl, alkenyl or alkynyl, and $R_{11}$ is hydrogen, alkyl, alkenyl or alkynyl, when Q is Q20.

8. A herbicidal composition, characterized in that it contains at least one compound according to claim 1 and an agricultural adjuvant.

9. A method for controlling undesired vegetation which comprises applying to a locus to be protected a herbicidally effective amount of a compound of claim 1.

10. The method of claim 9 wherein the locus to be protected is a cereal crop field.

11. The method of claim 9 wherein the compound of claim 1 is applied to soil as a preemergent herbicide.

12. The method of claim 9 wherein the compound of claim 1 is applied to plant; foliage.

* * * * *